US010842819B2

(12) United States Patent
Ushijima et al.

(10) Patent No.: US 10,842,819 B2
(45) Date of Patent: Nov. 24, 2020

(54) COMPOSITIONS AND METHODS FOR TREATING ITCHING, GINGIVOSTOMATITIS, AND DEMODECTIC MANGE

(71) Applicant: CMI Research Management, LLC, Honolulu, HI (US)

(72) Inventors: Ryan Ushijima, Honolulu, HI (US); Richard N. Ushijima, Wahaiwa, HI (US)

(73) Assignee: CMI Research Management, LLC, Honolulu, HI (US)

( * ) Notice: Subject to any disclaimer, the term of this patent is extended or adjusted under 35 U.S.C. 154(b) by 420 days.

(21) Appl. No.: 15/206,145

(22) Filed: Jul. 8, 2016

(65) Prior Publication Data

US 2017/0035810 A1 Feb. 9, 2017

Related U.S. Application Data

(63) Continuation-in-part of application No. PCT/US2015/010518, filed on Jan. 7, 2015.

(60) Provisional application No. 61/925,594, filed on Jan. 9, 2014, provisional application No. 62/330,778, filed on May 2, 2016.

(51) Int. Cl.
*A61K 36/00* (2006.01)
*A61K 35/26* (2015.01)
*A61K 35/20* (2006.01)
*A61K 31/7048* (2006.01)
*A61K 45/06* (2006.01)

(52) U.S. Cl.
CPC .......... *A61K 35/26* (2013.01); *A61K 31/7048* (2013.01); *A61K 35/20* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 4,548,813 A | 10/1985 | Lawson | |
| 4,772,588 A | 9/1988 | Scioppacassi | |
| 4,814,434 A * | 3/1989 | Goldfarb | A61K 35/26 424/580 |
| 4,826,680 A * | 5/1989 | Jaeger | A61K 35/26 424/580 |
| 5,032,408 A | 7/1991 | Schreuder | |
| 5,750,149 A | 5/1998 | Gobbi | |
| 8,071,716 B2 | 12/2011 | Devary | |
| 8,609,824 B2 | 12/2013 | Ushijima | |
| 2003/0149090 A1 | 8/2003 | Gehlsen | |
| 2010/0166789 A1 | 7/2010 | Keledjian | |
| 2011/0020461 A1 * | 1/2011 | Leneau | A61K 31/728 424/353 |
| 2011/0319321 A1 * | 12/2011 | Saharan | A61K 35/20 514/3.8 |
| 2013/0274177 A1 | 10/2013 | Saharan | |

OTHER PUBLICATIONS

"Symptoms of Ringworm Infections," Centers for Disease Control and Prevention, Dec. 6, 2015, <https://www.cdc.gov/fungal/diseases/ringworm/symptoms.html> [retrieved Aug. 14, 2017], 2 page.
Tosti, A., MD., et al., "Contact Stomatitis Clinical Presentation," Medscape, <http://emedicine.medscape.com/article/1076589-clinical> [retrieved Aug. 14, 2017], 1 page.
International Search Report and Written Opinion dated Aug. 1, 2017, in International Patent Application No. PCT/US2017/029961, filed Apr. 27, 2017, 13 pages.
Belgard, S., et al., "Relevance of Feline Calicivirus, Feline Immunodeficiency Virus, Feline Leukemia Virus, Feline Herpesvirus and Bartonella Henselae in Cats With Chronic Gingovistomatitis," Bed Munch Tierarztl Wochenschr. 123 (9-10)369-376, Sep.-Oct. 2010, Abtract.
Bergesi, G., and R. Falchetti, "Chemical Characterization and Biological Activity of a New Thymic Extract," Folia Allergol Immunol. Clin. 24:204-208, 1977.
Corbee, R.J., et al., "Inflammation and Wound Healing in Cats With Chronic Gingivitis/Stomatitis After Extraction of all Premolars and Molars Were Not Affected by Feeding of Two Diets With Different Omega-6/Omega-3 Polyunsaturated Fatty Acid Ratios," Journal of Animal Physiology and Animal Nutrition 96:671-680, 2010.
"Demodex (Manage Mite), Current Advise on Parasite Control: Ectoparasites—Demodex (Manage Mite)," Companion Animal Parasite Council, Mar. 2013, <http://www.capcvet.org/capc-recommendations/demodex-manage-mite/> [retrieved on Apr. 3, 2015], 6 pages.

(Continued)

*Primary Examiner* — Qiuwen Mi
(74) *Attorney, Agent, or Firm* — Barry L. Davison; Davis Wright Tremaine LLP

(57) ABSTRACT

Provided are methods for treating itching caused by allergy, include itching associated with parasite-mediated inflammation (e.g., demodicosis, stomatitis, dermatophytosis, etc.), comprising administration to a mammalian subject in need thereof a therapeutically effective amount of a heat-treated, fractionated thymus extract composition (e.g., Thyex-1-6A and -6B compositions, comprising proteins or polypeptides having molecular weights in the range of 3.5 kDa to 30 kDa), in combination with or formulated with colostrum, to provide for reducing itching in the subject. Combination or adjunctive therapies comprising administration of a heat-treated, fractionated thymus extract composition in combination with or formulated with colostrum, and including at least one additional anti-parasitic, anti-bacterial, anti-fungal, anti-viral agent, or homeopathic agent are also provided. Methods of treating parasite-mediated inflammation, comprising administration of fractionated thymus extract compositions to reduce parasite-mediated inflammation are provided.

63 Claims, 7 Drawing Sheets

(56) References Cited

OTHER PUBLICATIONS

Dolieslager, S.M.J., et al., "Identification of Bacteria Associated With Feline Chronic Gingivostomatitis Using Culture-Dependent and Culture-Independent Methods," Veterinary Microbiology 148:93-98, 2011.

Dowers, K.L., et al., "Association of Bartonella Species, Feline Calicivirus, and Feline Herpesvirus 1 Infection With Gingivostomatitis in Cats," Journal of Feline Medicine and Surgery 12:314-321, 2010.

Drazenovich, T.L., et al., "Effects of Dietary lysine Supplementation of Upper Respiratory and Ocular Disease and Detection of Infectious Organisms in Cats Within an Animal Shelter," American Journal of Veterinary Research 70 (11):1391-1400, Nov. 2009.

Goldstein, R.S., "Diseases of the Digestive System," in R.S. Goldstein (ed.), Integrating Complementary Medicine into Veterinary Practice John Wiley & Sons, Inc., 2008, Chapter 11, pp. 277-387.

Goldstein, A.L., and A. White, "Thymosin and Other Thymic Hormones: Their Nature and Roles in the Thymic Dependency of Immunological Phenomena," in A.J.S. Davies and R.L. Carter (eds.), Contemporary Topics in Immunobiology: vol. 2, Thymus Dependency, Plenum Press, New York-London, 1973, Chapter 20, pp. 339-350.

Hargis, A.M., and P.E. Ginn, "Feline Herpesvirus 1-Associated Facial and Nasal Dermatitis and Stomatitis in Domestic Cats," Veterinary Clinics of North America: Small Animal Practice 29(6):1281-1290, Nov. 1999.

Healey, K.A.E., et al., "Prevalence of Feline Chronic Gingivo-Stomatitis in First Opinion Veterinary Practice," Journal of Feline Medicine and Surgery 9:373-381, 2007.

Hennet, P.R., et al., "Comparative Efficacy of a Recombinant Feline Interferon Omega in Refractory Cases of Calicivirus-Positive Cats With Caudal Stomatitis: A Randomised, Multi-Centre, Controlled, Double-Blind Study in 39 Cats," Journal of Feline Medicine & Surgery 13(8):577-587, Aug. 2011.

Hooper, J.A., et al., "The Purification and Properties of Bovine Thymosin," Annals New York Academy of Sciences 249:125-144, Feb. 1975.

Ioannou, K., et al., "Prothymosin Alpha: A Ubiquitous Polypeptide With Potential Use in Cancer Diagnosis and Therapy," Cancer Immunology Immunotherapy 61(5):599-614, May 2012.

Krishnan, S.K., et al., "Synthesis, Antiviral and Cytotoxic Investigation of 2-Phenyl-3-Substituted Quinazolin-4(3H)-Ones," European Review for Medical and Pharmacological Sciences, 15(6):673-81, Jun. 2011.

Lee, M., et al., "Immonohistological Evaluation of Feline Herpesvirus-1 Infection in Feline Eosinophilic Dermatoses or Stomatitis," Journal of Feline Medicine and Surgery 12:72-79, 2010.

Lommer, M.J., and F.J.M. Verstraete, "Concurrent Oral Shedding of Feline Calicivirus and Feline Herpesvirus 1 in Cats With Chronic Gingivostomatitis," Oral Microbiology Immunology 18(2):131-134, Apr. 2003.

Ohno, N., et al., "Antitumor 1,3-β-Glucan From Cultured Fruit Body of Sparassis Crispa," Biological and Pharmaceutical Bulletin 23(7):866-872, Jul. 2000.

International Search Report and Written Opinion dated Mar. 25, 2015, in International Patent Application No. PCT/US2015/010518, filed Jan. 7, 2015, 23 pages.

\* cited by examiner

COMPOSITIONS AND METHODS FOR TREATING ITCHING, GINGIVOSTOMATITIS, AND DEMODECTIC MANGE

CROSS-REFERENCE TO RELATED APPLICATION(S)

This application claims the benefit of priority to U.S. Provisional Application No. 62/330,778, filed May 2, 2016, and entitled "COMPOSITIONS AND METHODS FOR TREATING ITCHING CAUSED BY ALLERGY," and this application is a Continuation-in-Part of PCT/US2015/010518, filed Jan. 7, 2015 (published as WO 2015/105905), which claims the benefit of priority to U.S. Provisional Application No. 61/925,594, filed Jan. 9, 2014, and entitled "COMPOSITIONS AND METHODS FOR TREATING GINGIVOSTOMATITIS AND DEMODECTIC MANGE," all of which are incorporated by reference herein in their entireties.

TECHNICAL FIELD OF THE INVENTION

Aspects of the present invention relate generally to the use of thymus extract compositions (e.g., Thyex-1-Thyex 6A and Thyex-6B; Kyosenex® as described herein) used in combination with or formulated with colostrum for treating itching caused by allergy, including itching caused by inflammation related to the presence of mammalian parasites and/or viral infections, and in more particular veterinary aspects to treating itching caused by allergy, and itching associated with demodectic mange and stomatitis (e.g., gingivostomatitis) in the veterinary setting (e.g., treating canine, feline, bovine, equine, ovine, porcine, avian, etc., disorders). Combination or adjunctive therapies of the thymus extract compositions with colostrum (e.g., bovine colostrum) are encompassed, as well as those using at least one additional anti-parasitic, anti-bacterial, anti-fungal, anti-viral agent, or homeopathic agent.

BACKGROUND

Itchy skin. Itchy skin (e.g., pruritus, dermatitis, eczema, psoriasis, dermatographism, etc.), is an irritating and uncontrollable sensation that makes you want to scratch to relieve the feeling. The possible causes for itchiness range from internal illnesses, such as kidney or liver disease, to skin rashes, allergies, and dermatitis. Itching caused by allergy is a huge problem, particularly in the veterinary setting, and including that associated with demodectic mange and stomatitis (e.g., gingivostomatitis) in the veterinary setting (e.g., treating canine, feline, bovine, equine (e.g., race horse), ovine, porcine, etc., disorders). Itching can be caused by viruses (chicken pox, measles) and other agents (e.g., fungus, mites, bedbugs, lice, pinworms, scabies, etc.).

Colostrum. Colostrum is the lacteal (mammary) secretion of mammals, produced immediately prior to birth and intended for feeding to the newborn. It is rich in protective and regulating factors necessary to promote health and vitality. It is nature's most concentrated source of biologically active components, particularly in the first, second and third milkings (e.g., with about 72 hours postpartum) It has existed since the first mammals roamed the planet and used by humans of various cultures for thousands of years. Cows are an ideal source of colostrum for at least the three following basic reasons: (i) nutritional, management and health improvements of dairy cows have led to greater colostrum production during the past 100 years. The calf's needs are always fulfilled first. Only surplus colostrum can be humanely harvested for other purposes; (ii) bovine colostrum is more potent than human colostrum in many regards. Newborn human infants have more competent immune function due to placental transfer of antibodies and various proteins/peptides which do not occur in ruminants (mammals with four chambered stomachs such as cows, goats and sheep). Because of this, these factors are concentrated and retained in the bovine colostrum for feeding to the calf immediately after birth; and (iii) the biologically active components are either identical or functionally identical regardless of the species of origin or use. In the first milking collected within six hours, over 80% of the albumin fraction is bioactive components produced in the bone marrow and circulatory system. At the second milking collected between 12 and 24 hours, only 50% is considered bioactive. Production of the whey proteins beta-lactoglobulin and alpha lactalbumin produced from amino acids in the alveoli of the mammary gland now account for the majority of the protein. While they have biological function in addition to their primarily nutritional role, these proteins are available in many consumer foods, whey protein concentrates and isolates. When the transition to milk has been completed, the bio-actives are less than 1% of that contained in colostrum. Because the transfer of all factors is not diminished at the same rate during the period after birth, 1st milking bovine colostrum has a different balance (ratio) of factors compared to the subsequent transitional period milkings.

Thymus extracts. Thymus extract compositions (e.g., Thyex-1-Thyex 6A and Thyex-6B; Kyosenex® are described herein.

Demodicosis (Demodectic Mange). Itching is a big problem with, for example, Demodicosis, also called demodectic mange or red mange, is caused by a sensitivity to *Demodex* mites (in the family Demodicidae) when the animal's immune system is unable to control the mites. *Demodex canis*, for example, occurs naturally in the hair follicles of most dogs in low numbers around the face and other areas of the body. In most dogs, these mites never cause problems. However, in certain situations (e.g., underdeveloped or impaired immune system, intense stress, or malnutrition, the mites can reproduce rapidly, causing symptoms in sensitive dogs that range from mild irritation and hair loss on a small patch of skin to severe and widespread inflammation, secondary infection, and in rare cases can be a life-threatening condition. Small patches of demodicosis often correct themselves over time as the dog's immune system matures, although treatment is usually recommended. Minor cases of demodectic mange usually do not cause much itching but might cause pustules on the dog's skin, redness, scaling, leathery, hair loss, warm to the touch, or any combination of these. It most commonly appears first on the face, around the eyes, or at the corners of the mouth, and on the forelimbs and paws. Minor cases of demodectic mange may be misdiagnosed as a "hot spot" or other skin ailment. In the more severe form, hair loss can occur in patches all over the body and might be accompanied by crusting, pain, enlarged lymph nodes, and deep skin infections. Demodectic mange is transmitted from host to host through direct contact. Typically animals become infected through nursing from their mother. *Demodex* mites are host-adapted; there is no zoonotic potential in either canine or feline demodicosis. These mites (e,g., *Demodex canis*) thrive only on their specific hosts (dogs). The transmission of these mites from mother to pup, for example, is typical, but some individuals are sensitive to the mites due to a cellular immune deficiency, underlying disease, stress, or malnutrition, which can lead to the development of clinical demodectic mange. Some breeds appear to have an increased risk of mild cases as young dogs, including the Afghan Hound, American Staffordshire Terrier, Boston Terrier, Boxer, Chihuahua, Chow Chow, Shar Pei, Collie, Dalmatian, Doberman Pinscher, Bulldog, French Bulldog, English Bull Terrier, Miniature Bull Terrier, German Shepherd Dog, Great Dane, Old English Sheepdog, American Pit Bull Terrier, West Highland White Terrier, Rat Terrier, Yorkshire Terrier, and Pug. Demodectic mange also occurs in other domestic and wild animals. The mites are specific to their hosts, and each mammal species is host to one or two unique species of *Demodex* mites. There are two types of demodectic mange in cats. *Demodex cati* causes follicular mange, similar to that seen in dogs, though it is much less common. *Demodex gatoi* is a more superficial form of mange, causes an itchy skin condition, and is contagious amongst cats. These diseases in humans are usually caused by *Demodex folliculorum* (not the same species affecting dogs) and are usually called demodicosis which may have a rosacea-like appearance. Common symptoms include hair loss, itching and inflammation. An association with *pityriasis folliculorum* has also been described.

If treatment is deemed necessary Goodwinol, a rotenone-based insecticide ointment is often prescribed, but it can be irritating to the skin. Demodectic mange with secondary infection is treated with antibiotics and medicated shampoos. In more severe generalized cases, Amitraz is a parasiticidal dip that is licensed for use in many countries (the only FDA approved treatment in the USA) for treating canine demodicosis. It is applied weekly or biweekly, for several weeks, until no mites can be detected by skin scrapings. Demodectic mange in dogs can also be managed with avermectins, although there are few countries which license these drugs, which are given by mouth, daily, for this use. Ivermectin is used most frequently; collie-like herding breeds often do not tolerate this drug due to a defect in the blood-brain barrier, though not all of them have this defect. Other avermectin drugs that can be used include doramectin and milbemycin. Cats with *Demodex gatoi* must be treated with weekly or bi-weekly sulfurated lime rinses. *Demodex cati* are treated similarly to canine demodicosis. Because of the possibility of the immune deficiency being an inherited trait, many veterinarians believe that all puppies with generalized *demodex* should be spayed or neutered and not reproduce. Females with generalized *demodex* should be spayed because the stress of the estrus cycle will often bring on a fresh wave of clinical signs. For really bad cases, the animal must be euthanized.

Forms of demodicosis include localized demodicosis, usually in juvenile dogs, occurs as isolated scaly bald patches, usually on the dog's face, but occasionally elsewhere. It is considered common and the majority of cases resolve with no treatment of any kind. Localized disease does not involve more than two body regions (One spot or two on the face and one spot or two on a leg would still qualify as localized even though the spots are not close together). Localized disease involves no more than four spots total on the dog. Generalized demodicosis can be very difficult, and requires persistent intervention and dedicated owners, as it is multifactorial and is often complicated by concurrent infections. Demodectic Pododermatitis is a very resistant type, confined to the paws, and often accompanied by bacterial infections, as the foot is the last stronghold of the mite. Old English Sheepdogs and Shar Peis tend to get severe forms of this condition. Sarcoptic mange, which is caused by the deeply burrowing mite, *Sarcoptes scabiei*, is extremely contagious between dogs, and can be transmitted to people. It is the mange most people picture when the think of a "mangy dog". Dogs are highly pruritic, with progressive hair loss, reddened skin, and scabbing especially on ear flaps, eyes, elbows, feet, and chest. It is often difficult to detect on skin scrapings, so it often better to treat on clinical signs, even in the presence of a negative scraping.

Dermatophytosis. Ringworm "dermatophytosis," is a fungal infection affecting the skin, hair and occasionally nails of animals (and people). Three species of ringworm fungus most commonly affect cats and dogs. *Microsporum canis, Trichophyton mentagrophytes,* and *Microsporum gypseum.*

Gingivostomatitis. Stomatitis is inflammation in the mouth, and is also associated with irritation and itching. The term stomatitis refers to any inflammatory process affecting the mucous membranes of the mouth and lips, with or without oral ulceration. The inflammation can be caused by conditions in the mouth itself, such as poor oral hygiene, dietary protein deficiency, poorly fitted dentures, or from mouth burns and scars from food or drinks, toxic plants, or by conditions that affect the entire body, such as medications, allergic reactions, radiation therapy, or infections. The term gingivostomatitis, refers to inflammation of the gingiva (i.e., gingivitis) and the mouth generally.

Cats with this chronic, painful inflammatory disease can be severely compromised, and medical treatment can cause adverse effects.

Affected cats exhibit a variety of clinical signs including partial to complete anorexia, ptyalism, halitosis, weight loss, abnormal swallowing, scratching, and oral pain. Physical examination results show gingivitis, stomatitis, and possibly palatitis, glossitis, cheilitis, pharyngitis, and mandibular lymphadenopathy. Oral inflammation is often extensive, and affected tissues are typically ulcerated, proliferative, and hyperemic. All breeds of cat have the potential to develop the disease, including domestic shorthaired cats. And cats can become affected at any age. Gingivostomatitis is not an infection but rather an inflammation. The inflammatory lesions associated with feline gingivostomatitis are thought to be the result of a highly reactive immune system. The specific antigen that the immune system is reacting to is not easily identified and is often unknown. Antigens that may have a role in triggering the oral inflammation associated with feline gingivostomatitis include viral, food, or environmental antigens. Autoimmunity may also be a component of the disease. Herpetic gingivostomatitis is inflammation of the mouth caused by herpes simplex virus. Allergic gingivostomatitis, or allergic contact gingivostomatitis.

Treatment may include, for example, at least one of antibiotics, medicated mouth rinses, salt water, hydrogen peroxide, Xylocaine, antiviral agents, Acyclovir, fluid intake, good oral hygiene, gentle debridement of the mouth, etc.

For really bad cases, the animal's teeth must be pulled and they often succumb to starvation and dehydration because of pain in the mouth.

Both demodicosis and stomatitis in mammals, animals (e.g., in dogs and cats, etc.) have no effective treatment for the bad cases, including for itching associated therewith. There is a pronounced need in the art for economically viable treatments for demodicosis and stomatitis (e.g., gingivostomatitis) in animals (e.g., veterinary therapies), and to relieve the itching associated with such conditions.

SUMMARY OF THE INVENTION

Particular aspects provide methods for treating itching (e.g., allergic itching), including itching associated with gingivostomatitis and demodectic mange, comprising administration of proprietary thymus extracts (e.g., Thyex-1-6A and -6B; see working EXAMPLES 1-8 herein) used in combination with, or formulated with colostrum, where, for example, such administration provides for lessening, alleviating and/or halting and/or permanent reversal of itching symptoms, and for temporary and long-term relief for itching. In preferred embodiments, the treatment with thymus extract compositions, comprises administration of Kyosenex® prepared in accordance with working EXAMPLES 1 or 2 herein, and formulated with colostrum (e.g., bovine colostrum; first, second or third milking colostrums, or within 72 hours postpartum; preferably first milking colostrum is used for the formulations).

Particular aspects provide methods for treating inflammation associated with gingivostomatitis and demodectic mange inflammation, comprising administration of proprietary thymus extracts (e.g., Thyex-1-6A and -6B; see working EXAMPLES 1-8 herein), where, for example, such administration provides for lessening, alleviating and/or halting and/or permanent reversal of *demodex* symptoms, and for temporary and long-term relief for feline stomatitis. In preferred embodiments, the treatment with thymus extract comprises stimulating or modulating the immune system by administration of Kyosenex® prepared in accordance with working EXAMPLES 1 or 2 herein.

In particular embodiments of the present invention, the methods are practiced by administration of at least one of thymus extracts Thyex-1-6A and -6B (see working EXAMPLES 1-8 herein) used in combination with or formulated with colostrum, and therapeutic compositions comprising said Thyex/colostrum formulations. Preferably, the composition is Kyosenex® (a heat-treated, fractionated thymus extract composition comprising proteins or polypeptides having molecular weights in the range of 3.5 kDa to 30 kDa; see Applicant's U.S. Pat. No. 8,609,824), preferably prepared as describe under EXAMPLES 1 or 2 herein, although Kyosenex® can be prepared in accordance with any of EXAMPLES 1-8, providing a heat-treated, fractionated thymus extract composition comprising proteins or polypeptides having molecular weights in the range of 3.5 kDa to 30 kDa.

Preferably, preparing thymus extract compositions (Thyex-1-6A and -6B as provided under EXAMPLES 1-8 herein) comprises: homogenizing thymus tissue; removing tissue debris therefrom to produce a supernatant; and concentrating and denaturing the supernatant to produce a clarified supernatant fraction. Preferably, the processes comprise further clarifying of the clarified supernatant by high-speed centrifugation at about 8,500 (g). Preferably the processes further comprise filter sterilizing. Preferably, the pH and ionic strength of the resulting supernatant are physiologically compatible. Preferably, the pH and ionic strength of the resulting supernatant have values of about 7 and of about 0.85% (w/v), respectively. Preferably, the initial ratio of thymus tissue to aqueous homogenization fluid is about 350 g wet weight of thymus tissue to about 0.7 L of homogenization fluid. Preferably, the processes comprise further fractionating based on molecular weight to obtain a final fraction having proteins of about 3.5 to about 30 kDa.

Additional embodiments for preparing thymus extract compositions comprise: homogenizing thymus tissue; removing tissue debris therefrom to produce a supernatant; concentrating, denaturing, and clarifying the supernatant fraction; further concentrating the clarified supernatant fraction to produce a further concentrated fraction; fractionating the further concentrated fraction to remove molecules having a molecular weight less than about 3.5 kDa; and further fractionating based on molecular weight to obtain a final fraction having proteins of about 3.5 to about 30 kDa. Preferably, the processes further comprise adjusting the pH and/or ionic strength, of the final fraction to a physiological or therapeutically compatible value. Preferably, said adjusting is achieved by adding phosphate buffer and/or sodium chloride to produce a solution having a pH value of about 7, and/or an ionic strength of about 0.85% (w/v). Preferably the processes further comprise filter sterilizing. Preferably, said sterilizing is achieved by using a 0.2 micron membrane filter. Preferably, the initial ratio of thymus tissue to aqueous homogenization fluid is about 350 g wet weight (about 400 ml) of thymus tissue to about 0.7 L of homogenization fluid.

Yet further embodiments provide pharmaceutical compositions comprising: thymus extract compositions (Thyex-1-6A and -6B) formulated with colostrum produced in accordance with the above-described processes, and a pharmaceutically acceptable carrier. Preferably, the thymus extract composition Kyosenex® is used. Preferably, bovine colostrum; first, second or third milking colostrums, or within 72 hours postpartum are used; preferably first milking colostrum is used for the formulations.

In particular aspects, the subject mammal treated includes, but is not limited to human, canine, feline, bovine, equine, ovine, and porcine. Avian is also encompassed.

According to additional aspects, the inventive Thyex compositions are useful for immunostimulation and/or immunoregulation, comprising administering to a mammalian subject in need thereof a therapeutically effective amount of a thymus extract composition (Thyex-1-6A and -6B) produced in accordance with the herein-described processes. According to further aspects, the inventive Thyex compositions are useful for modulating endocrine function, comprising administering to a mammalian subject in need thereof a therapeutically effective amount of a thymus extract composition (Thyex-1-6A and -6B) produced in accordance with the herein-described processes.

According to still further aspects, the inventive Thyex compositions are useful for treating or preventing, virus infection, virus-associated conditions or secondary infection, comprising administering a therapeutically effective amount of a thymus extract composition (Thyex-1-6A and -6B) produced in accordance with the herein-described processes.

According to certain aspects, the inventive Thyex compositions are used in combination with administering of at least one additional anti-parasitic, anti-microbial agent (e.g., an antibiotic), antifungal agent, antiviral agent, or homeopathic agent.

According to additional aspects, the inventive Thyex/colostrum formulations are useful for reducing itching, comprising administering to a mammalian subject in need thereof a therapeutically-effective amount of a thymus extract composition (Thyex-1-6A and -6B)/colostrum formulation produced in accordance with the herein-described processes. According to further aspects, the inventive Thyex/colostrum formulations are useful for reducing itching, comprising administering to a mammalian subject in need thereof a therapeutically effective amount of a thymus extract composition (Thyex-1-6A and -6B)/colostrum formulation produced in accordance with the herein-described processes.

According to certain aspects, the inventive Thyex/colostrum formulations are used in combination with administering of at least one additional anti-parasitic, anti-microbial agent (e.g., an antibiotic), antifungal agent, antiviral agent, or homeopathic agent.

Provided are methods for treating itching, comprising administration to a subject (e.g, mammalian subject) in need thereof a therapeutically effective amount of a heat-treated, fractionated thymus extract composition in combination with or formulated with colostrum, to provide for reducing itching in the subject, wherein a method for treating itching is afforded. The methods can be applied, for example, to itching caused by allergy or itching caused by parasites, including situations wherein the parasite-mediated itching comprises itching in demodicosis (demodectic mange; e.g., canine demodicosis, including that caused by *Sarcoptes scabiei*; e.g., feline demodicosis caused by *Demodex cati* or by *Demodex gatoi*. The methods can also be applied to parasite-mediated itching comprising itching in stomatitis (e.g., wherein the stomatitis is gingivostomatitis) or itching in dermatophytosis (ring worm)).

In the methods, administration of the thymus extract/ colostrum combination or formulation is at least once or twice per day for at least two days, and may also be administered twice per day for at least two days, and then at least twice per week for at least one month, or may, for example be administered at least twice per day for at least a week.

In the thymus extract/colostrum combinations or formulation used in the methods, the thymus extract composition comprises proteins or polypeptides having molecular weights in the range of 3.5 kDa to 30 kDa.

In the thymus extract/colostrum combinations or formulation used in the methods, the colostrum is preferably bovine colostrum, for example, wherein the bovine colostrum comprises first milking colostrum, second milking colostrum or third milking colostrum (or within 72 hours postpartum).

In the methods, administration of the thymus extract/ colostrum combination or formulation may comprise treating with at least one additional anti-parasitic, anti-bacterial, anti-fungal, anti-viral agent, or homeopathic agent. For example, wherein at least one anti-parasitic agent comprises an avermectin (e.g., ivermectin, doramectin and/or n; preferably ivermectin). For example, wherein the at least one anti-bacterial agent comprises an antibiotic, metronidazole, tinidazole, co-trimoxazole, cephamandole, ketoconazole, latamoxef, cefoperazone, amoxicillin, cefmenoxime, furazolidone, doxycycline and erythromycin. For example, wherein the at least one anti-fungal agent comprises one or more of itraconazole, Terbinafine (Lamasil), clotrimazole (Lotrimin, Mycelex), fluconazole, ketoconazole (Spectazole), griseofulvin, econazole (Spectazole), miconazole, miconazole nitrate (Monistat-Derm), tolnaftate, thiabendazole (Tresaderm), lime-sulfur treatments, imidazoles, (eg., bifonazole, butoconazole, fenticonazole, isoconazole, oxiconazole, sertaconazole, sulconazole, and tioconazole), triazoles, fluconazole, itraconazole, isavuconazole, ravuconazole, posaconazole, voriconazole, and terconazole), thiazoles, abafungin, allylamines, terbinafine, amorolfine, naftifine, and butenafine, and echinocandins, anidulafungin, caspofungin, and micafungin. For example, wherein the at least one anti-viral agent comprises at least one of combivir, boceprevir, abacavir, docosanol, aciclovir, didanosine, cidofovir, acyclovir, delavirdine, adefovir, amantadine, amprenavir, arbidol, darunavir atazanavir, atripla, zanamivir, or oseltamivir. For example, wherein the at least one homeopathic agent comprises at least one of traumeel, homotox, SBGA (blue green algae), placenta, wobenzyme, spascupreel, formula, yunnan paiyo, vitamin E, omega-3 fatty acids, semongrass oil, and cedar oil.

Administration of the thymus extract/colostrum combination or formulation is preferably oral, but may be at least one route selected from the group consisting of oral administration, injection, inhalation, topical application, and rectal administration.

Compositions, including therapeutic compositions, comprising a thymus extract in combination with colostum are provided, preferably wherein the thymus extract and the colostrum are bovine. In the compositions, it is preferred that the thymus extract comprises proteins or polypeptides having molecular weights in the range of 3.5 kDa to 30 kDa, and that the bovine colostrum comprises first milking colostrum. Compositions may alternately, or additionally comprise second or third milking colostrums (preferably within 72 hours postpartum).

DETAILED DESCRIPTION OF THE INVENTION

Figure 1:
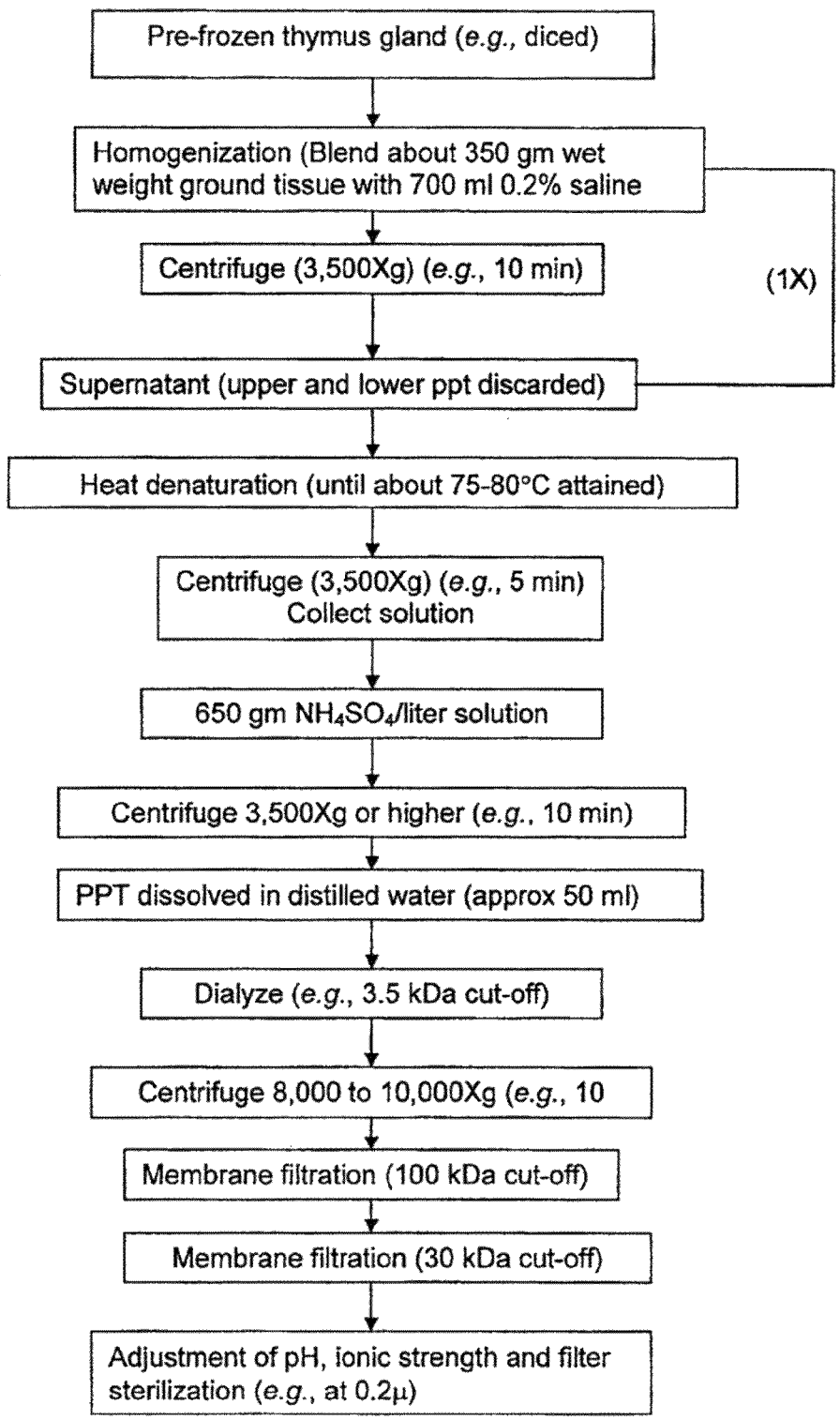
FIG. 1 is a flow diagrammatic representation comprising an inventive Thyex-1 process embodiment for preparing a thymus extract composition.
Figure 2:
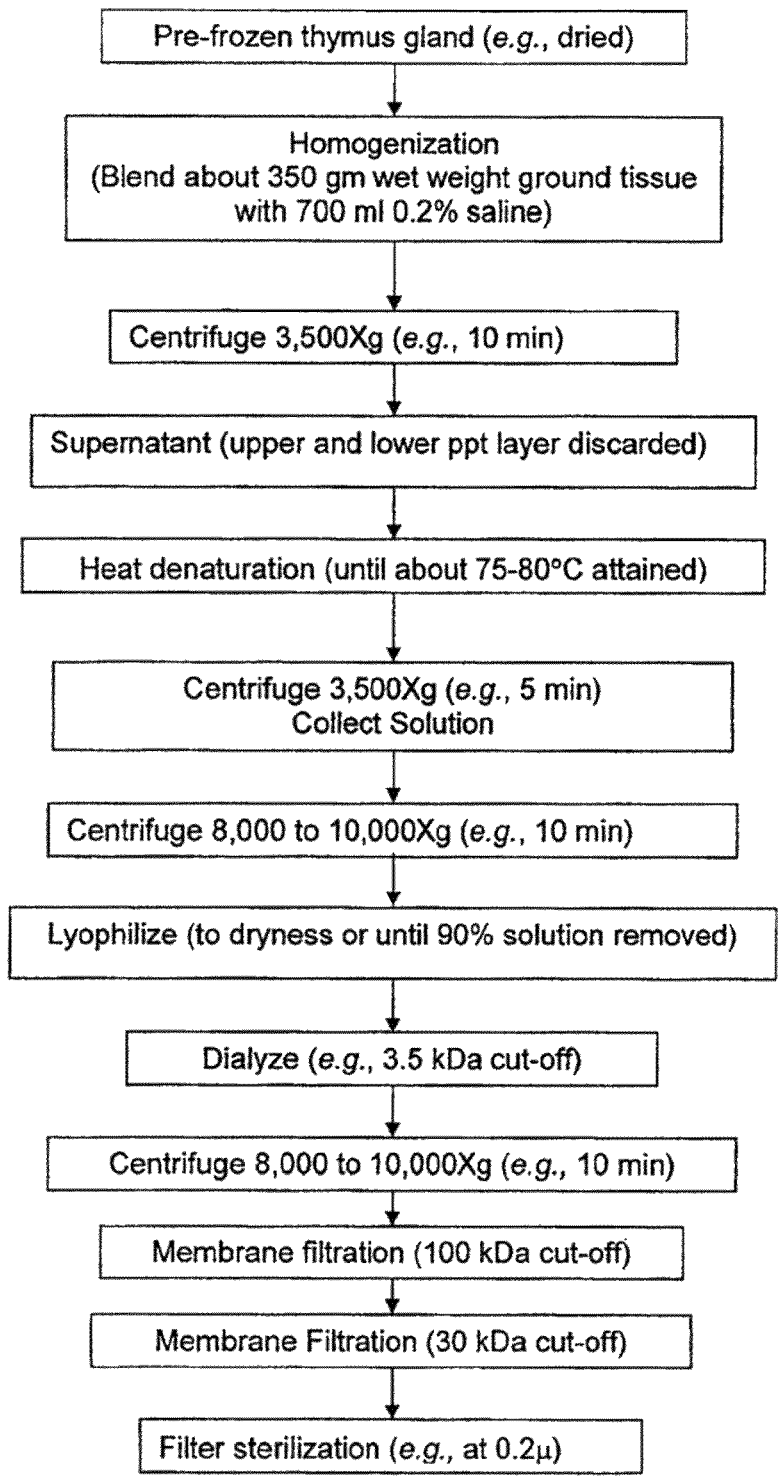
FIG. 2 is a flow diagrammatic representation comprising an inventive Thyex-2 process embodiment for preparing a thymus extract composition.
Figure 3:
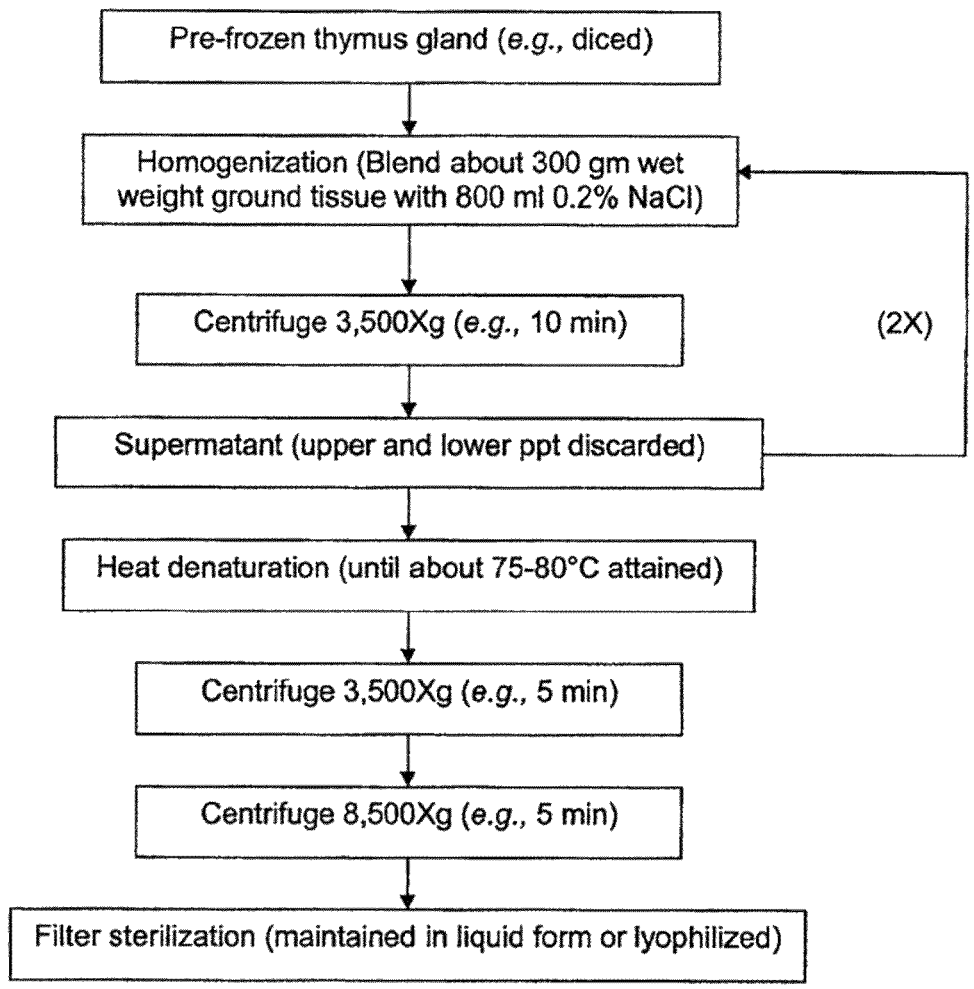
FIG. 3 is a flow diagrammatic representation comprising an inventive Thyex-3 process embodiment for preparing a thymus extract composition.

Aspects of the present invention provide methods for treating itching caused by allergy, and including itching cause by parasite-mediated inflammation, comprising administration to a mammalian subject in need thereof a therapeutically effective amount of a heat-treated, fractionated thymus extract composition in combination with colostrum, to provide for reducing itching, including allergic and parasite-mediated itching in the subject, wherein treating itching is afforded. In particular aspects, the heat-treated, fractionated thymus extract composition comprises proteins or polypeptides having molecular weights in the range of 3.5 kDa to 30 kDa.

In particular aspects, the itching is allergic itching, including allergic itching relating to parasite-mediated inflammation in demodectic mange (demodicosis) caused by sensitivity to *Demodex* mites, and treating itching relating to demodicosis is afforded. In certain embodiments, the demodicosis is that of canine demodicosis (e.g., that caused by *Sarcoptes scabiei*), or feline demodicosis (e.g., feline demodicosis caused by *Demodex cati* or by *Demodex gatoi*. In particular aspects, the parasite-mediated itching comprises itching in stomatitis, and wherein treating stomatitis related itching is afforded. In certain aspects the stomatitis is gingivostomatitis, and treating gingivostomatitis itching is afforded. In particular aspects, the parasite-mediated itching comprises itching in dermatophytosis (ring worm), and treating dermatophytosis itching is afforded.

In particular aspects, the heat-treated, fractionated thymus extract composition, for example, formulated with colostrum, is administered at least once. In particular aspects, the heat-treated, fractionated thymus extract colostrum formulation c is administered at least once per day orally for at least 5 day to one month. In certain embodiments, the heat-treated, fractionated thymus extract colostrum formulation is administered twice per day for at least 2 days, and then once per day for at least one week. In particular aspects, the heat-treated, fractionated thymus extract colostrum formulation is administered twice per week for at least one month.

Certain aspects of the above methods further comprise treating with at least one additional anti-parasitic, anti-bacterial, anti-fungal, anti-viral agent, and/or with a homeopathic agent. In certain aspects, the at least one anti-parasitic agent comprises an avermectin (e.g., comprises at least one of ivermectin, doramectin and milbemycin); preferably, ivermectin. In certain aspects, the at least one anti-bacterial agent comprises an antibiotic. In certain aspects, the at least one anti-fungal agent comprises one or more of itraconazole, Terbinafine (Lamasil), clotrimazole (Lotrimin, Mycelex), Fluconazole, ketoconazole (Spectazole), griseofulvin, econazole (Spectazole), miconazole, miconazole nitrate (Monistat-Derm), tolnaftate, thiabendazole (Tresaderm), or lime-sulfur treatments. In certain aspects, the at least one anti-viral agent comprises acyclovir. In certain aspects, the at least one homeopathic agent comprises at least one of traumeel, homotox, SBGA (blue green algae), placenta, wobenzyme, spascupreel, IMM formula, yunnan paiyo, vitamin E, omega-3 fatty acids, semongrass oil, and cedar oil.

In preferred aspects, the inventive compositions (Thyex-1-6A and -6B; Kyosenex®) are administered in combination with (or formulated with) the colostrum, and administering of at least one additional anti-parasitic, anti-microbial agent (e.g., an antibiotic), antifungal agent, antiviral agent, or homeopathic agent is also encompassed.

Aspects of the present invention provide methods for treating parasite-mediated inflammation, comprising administration to a mammalian subject in need thereof a therapeutically effective amount of a heat-treated, fractionated thymus extract composition, to provide for reducing parasite-mediated inflammation in the subject, wherein treating parasite-mediated inflammation is afforded. In particular aspects, the heat-treated, fractionated thymus extract composition comprises proteins or polypeptides having molecular weights in the range of 3.5 kDa to 30 kDa.

In particular aspects, the parasite-mediated inflammation comprises inflammation in demodectic mange (demodicosis) caused by sensitivity to *Demodex* mites, and treating demodicosis is afforded. In certain embodiments, the demodicosis is that of canine demodicosis (e.g., that caused by *Sarcoptes scabiei*), or feline demodicosis (e.g., feline demodicosis caused by *Demodex cati* or by *Demodex gatoi*. In particular aspects, the parasite-mediated inflammation comprises inflammation in stomatitis, and wherein treating stomatitis is afforded. In certain aspects the stomatitis is gingivostomatitis, and treating gingivostomatitis is afforded. In particular aspects, the parasite-mediated inflammation comprises inflammation in dermatophytosis (ring worm), and treating dermatophytosis is afforded.

In particular aspects, the heat-treated, fractionated thymus extract composition is administered at least once. In particular aspects, the heat-treated, fractionated thymus extract composition is administered at least once per month for at least one month. In certain embodiments, the heat-treated, fractionated thymus extract composition is administered at least once per week for at least one month. In particular aspects, the heat-treated, fractionated thymus extract composition is administered at least twice per week for at least one month.

Certain aspects of the above methods further comprise treating with at least one additional anti-parasitic, anti-bacterial, anti-fungal, anti-viral agent, and/or with a homeopathic agent. In certain aspects, the at least one anti-parasitic agent comprises an avermectin (e.g., comprises at least one of ivermectin, doramectin and milbemycin); preferably, ivermectin. In certain aspects, the at least one anti-bacterial agent comprises an antibiotic. In certain aspects, the at least one anti-fungal agent comprises one or more of itraconazole, Terbinafine (Lamasil), clotrimazole (Lotrimin, Mycelex), Fluconazole, ketoconazole (Spectazole), griseofulvin, econazole (Spectazole), miconazole, miconazole nitrate (Monistat-Derm), tolnaftate, thiabendazole (Tresaderm), or lime-sulfur treatments. In certain aspects, the at least one anti-viral agent comprises acyclovir. In certain aspects, the at least one homeopathic agent comprises at least one of traumeel, homotox, SBGA (blue green algae), placenta, wobenzyme, spascupreel, IMM formula, yunnan paiyo, vitamin E, omega-3 fatty acids, semongrass oil, and cedar oil.

In preferred aspects, the inventive compositions (Thyex-1-6A and -6B; Kyosenex®) are administered in combination with administering of at least one additional anti-parasitic, anti-microbial agent (e.g., an antibiotic), antifungal agent, antiviral agent, or homeopathic agent.

Particular aspects (see Applicant's U.S. Pat. No. 8,609,824; incorporated by reference herein in its entirety) provide a method for preparing heat-treated, fractionated thymus extract composition, comprising: homogenizing thymus tissue with aqueous homogenization fluid to produce an aqueous thymus homogenate; removing tissue debris from the aqueous thymus homogenate to produce a primary supernatant; heat denaturing the primary supernatant, and clarifying the denatured primary supernatant by use of at least one of low-speed centrifugation and filtration, to produce a clarified supernatant; and separating molecules having molecular weights less than about 3.5 kDa from the clarified supernatant, wherein a heat-treated, fractionated thymus extract composition lacking proteins or polypeptides having molecular weights less than about 3.5 kDa is provided. In certain aspects, the method further comprises separating molecules having molecular weights greater than about 30 kDa from the heat-treated, fractionated thymus extract composition, wherein a heat-treated, fractionated thymus extract composition comprising proteins or polypeptides having molecular weights in the range of about 3.5 kDa to about 30 kDa is provided. In certain embodiments, the method comprises further clarifying of the clarified supernatant by high-speed centrifugation to produce a final clarified supernatant fraction, and optionally sterilizing the final clarified supernatant fraction to produce a sterile final clarified supernatant fraction. In certain aspects, sterilizing is achieved by passing the final clarified supernatant fraction through a membrane filter. In particular embodiments, the initial ratio of thymus tissue to aqueous homogenization fluid is about 350 g wet weight of thymus tissue to about 0.7 of homogenization fluid. In certain aspects, removing tissue debris from the aqueous thymus homogenate is achieved by a combination of low-speed centrifugation and crude filtration. In certain aspects, heat denaturing and clarifying of the primary supernatant is achieved by heat denaturation, followed by low-speed centrifugation and crude filtration to remove particulate matter. In certain embodiments, the methods further comprise lyophilization of the final clarified supernatant fraction. Preferably no steps involving exogenously added protease digestion, or extraction with organic solvents are used.

Additional particular aspects provide a method for preparing a thymus extract composition, comprising: homogenizing thymus tissue with aqueous homogenization fluid to produce an aqueous thymus homogenate; removing tissue debris from the aqueous thymus homogenate to produce a primary supernatant; heat denaturing the primary supernatant, and clarifying the denatured primary supernatant by use of at least one of low-speed centrifugation and filtration to produce an intermediate clarified supernatant; concentrating the intermediate clarified supernatant to produce a concentrated intermediate fraction; and separating molecules having molecular weights less than about 3.5 kDa from the concentrated intermediate fraction, wherein a heat-treated, fractionated thymus extract composition lacking proteins or polypeptides having molecular weights less than about 3.5 kDa is provided. In certain embodiments, the method further comprises separating molecules having molecular weights greater than about 30 kDa from the heat-treated, fractionated thymus extract composition, wherein a heat-treated, fractionated thymus extract composition comprising proteins or polypeptides having molecular weights in the range of about 3.5 kDa to about 30 kDa is provided. Certain embodiments further comprise clarifying of the concentrated intermediate fraction by high-speed centrifugation to produce a final clarified supernatant fraction. Particular aspects further comprise adjusting at least one of the pH or ionic strength of the fraction having proteins or polypeptides of molecular weight of about 3.5 to about 30 kDa to a physiological or therapeutically compatible value, to produce a pH- or ionic strength-adjusted fraction, and in certain aspects, adjusting at least one of the pH or ionic strength to a physiological or therapeutically compatible value is achieved by adding phosphate buffer or sodium chloride to produce a fraction having at least one of a pH value of about 7 or an ionic strength of about 0.85% w/v. Certain embodiments further comprise sterilizing the pH-, or ionic strength-adjusted fraction to produce a sterile pH-, or ionic strength-adjusted fraction, and in particular aspects, sterilizing is achieved by passing the fraction through a membrane filter. In particular embodiments, the initial ratio of thymus tissue to aqueous homogenization fluid is about 350 g wet weight of thymus tissue to about 0.7 of homogenization fluid. In certain aspects, removing tissue debris from the aqueous thymus homogenate is achieved by a combination of low-speed centrifugation and crude filtration. For particular embodiments, heat denaturing and clarifying of the primary supernatant is achieved by heat denaturation, followed by low-speed centrifugation and crude filtration to remove particulate matter. In particular embodiments, concentrating the intermediate supernatant involves concentrating and fractionating, wherein the concentrating and fractionating is achieved by adding ammonium sulfate to the intermediate clarified supernatant, followed by low-speed centrifugation and suspension of the resulting ammonium sulfate pellet in an aqueous solution to provide a concentrated intermediate fraction. In particular aspects, separating molecules having molecular weights less than about 3.5 kDa from the concentrated intermediate fraction comprises dialysis of the concentrated intermediate fraction, followed by high-speed centrifugation to remove particulate matter, to provide for a clarified concentrated intermediate fraction lacking proteins or polypeptides having molecular weights less than about 3.5 kDa. In certain embodiments, separating molecules having molecular weights greater than about 30 kDa from the heat-treated, fractionated thymus extract composition, is achieved by passing the clarified concentrated intermediate fraction lacking proteins or polypeptides having molecular weights less than about 3.5 kDa consecutively through a first and a second membrane filter having exclusion limits of about 100 and about 30 kDa, respectively, and collecting the filtrate. Particular aspects further comprise lyophilization of the heat-treated, fractionated thymus extract composition comprising proteins or polypeptides having molecular weights in the range of about 3.5 kDa to about 30 kDa.

Yet additional particular aspects provide a composition or pharmaceutical composition, comprising a thymus extract composition, produced in accordance with the methods recited herein, in combination with Colostrum.

Particular embodiments further comprise administering a macrophage stimulating agent in combination with administration of the thymus extract/colostrum formulation for use in treating demodicosis and stomatitis (e.g., gingivostomatitis). In certain aspects, the macrophage stimulating agent comprises at least one of beta glucan, polysaccharides, toxoid vaccines, and Staph lysate vaccine, immune complexes, compliment components, lymphokinesm, tuftsin, lipopolysaccharides (LPS), muramyl dipeptide, physiologic cation complexing agents, pyran copolymers, polycarboxylates, ionphores, Quadrol (N,N,N',N'-tetrakis(2-hydroxypropyl)ethlenediamine), and macrophage stimlulating peptides. In certain aspects, the beta glucan comprises beta 1,3 glucan.

Further aspects provide a method for immunostimulation or immunoregulation, comprising administering to a mammalian subject in need thereof a therapeutically effective amount of a thymus extract/colostrum formulation produced in accordance with the methods recited herein, wherein at least one of immunostimulation or immunoregulation is afforded.

Yet further aspects provide a method for endocrine modulation, comprising administering to a mammalian subject in need thereof a therapeutically effective amount of a thymus extract/colostrum formulation produced in accordance with the methods recited herein, wherein endocrine modulation is afforded.

Definitions:

"Thymus extract" or thymus extract composition, refers to a composition produced in accordance with one or more of the Thyex-1, -2, -3, -4, -5, -6A, and -6B processes disclosed herein.

"Kyosenex®" as used herein, refers to a heat-treated, fractionated thymus extract composition comprising proteins or polypeptides having molecular weights in the range of 3.5 kDa to 30 kDa (e.g., see Applicant's U.S. Pat. No. 8,609,824), preferably prepared as described under EXAMPLES 1 or 2 herein, although Kyosenex® can be prepared in accordance with the methods described under any of EXAMPLES 1-8 herein, providing a heat-treated, fractionated thymus extract composition comprising proteins or polypeptides having molecular weights in the range of 3.5 kDa to 30 kDa. Preferably, Kyosenex® is made according to the method described under EXAMPLES 1 or 2. Typically, it is provided in a sterile vial containing 3-4 mg of lyophilized thymus extract.

"Colostrum," as used herein for adjunctive administration with thymus extracts, or for formulation of thymus extract compositions, refers to milking colostrum, and in particular aspects bovine colostrum is used. In preferred aspects, first milking bovine colostrum is used (e.g., "First Milking Bovine Colostrum" from Immuno-Dynamics, Fennimore, Wis.; sold as "ID-1" optionally with methyl paraben and/or propyl paraben as preservative). In additional aspects, second, third or even further milkings are used. In particular aspects, second and/or third milking colostrum is used (e.g., within 72 hours postpartum). Preferably, first milking colostrum is used. Most preferably, first milking bovine colostrum is used. In particular aspects, bovine colostrum is used to formulate the thymus extract for administration, and in certain embodiments, first milking bovine colostrum is used (e.g., "First Milking Bovine Colostrum™" from Immuno-Dynamics, Fennimore, Wis.; sold as "ID-1" optionally with methyl paraben and/or propyl paraben as preservative). According to particular aspects Kyosenex® PRIME is formulated (formulated for Applicant by Immuno-Dynamic & URL Laboratories, Fennimore, Wis. USA, using ID-1 serum ("Bovine IgG Colostrum Serum")) using 66.6 ug of Kyosenex/ml colostrum and administered in 7/10 ml (0.7 ml) per spray or dropwise, twice daily, 1 spray for each 15 lbs until resolution of condition, and then twice a week thereafter for maintenance.

"Animals" as used herein for treatment of subjects refers to, but are not limited to chicken, duck, fish, hamster, rat, guinea pig, human, canine, feline, bovine, equine (e.g., race horse), avian, ovine, goat, and porcine. Preferred animals are mammals.

"Anti-microbial agent" means an agent with, for example, antibacterial, antifungal, or antiviral activity, including, but not limited to: plant extracts (e.g., *Houttuynia cordata* extracts); antibiotics, such as β-lactam antibiotics, erythromycin compounds, Tetracycline compounds, aminoglycoside antibiotics, cephalosporin compounds, anthracycline compounds, phleomycin group antibiotics, sulfonamide compounds, macrolide antibiotics (e.g., tylosin, desmycosin, macrocin, and lactenocin), quinolone and quinolonyl compounds (e.g., quinolonyl lactams and quinolone thioureas, and carbacephem- and carbapenem-quinolones), and carbapenem compounds, along with those antibiotic agents more commonly used in the swine industry, such as lankacidin-group antibiotics and derivatives, diterpene antibiotics (e.g., tiamulin-type), polyether or polycyclic ether antibiotics and derivatives (e.g., A82810), lysocellin, treponemycin, antibiotic 10381b, antibiotics GE 37468 A, B, and C, A41030 antibiotics, antibiotic A47934, antibiotic BN-109, apramycin, actaplanin antibiotics, antibiotic A3823, antibiotic X-14766A, dihydromocimycin antibiotics, BM123☐-type antibiotics, antibiotic AV290, antibiotic A-32887, glycopeptide antibiotic UK-68,597, valnemulin, tiamulin, oxytetracyclin, chlortetracycline, tylosin, and manganese-containing antibiotic agents, copper-containing bleomycin group antibiotics; antifungal agents, such as partanamicins, fusacandins; and antihelminthic agents such as spiroketals, avermectin and milbemycin; and combinations thereof.

"Crude filtration" or "coarse filtration" means filtering a solution having particulate, precipitated, or flocculent suspended material through, e.g., one or more layers of standard cheese cloth, or other sieving device (e.g., screen, strainer, colander, etc.), to remove said material.

"Low-speed centrifugation" means centrifugation at about 3,500×g (±5% or ±10%) for about 5-10 minutes (±5% or ±10%), or an equivalent sedimentation protocol thereof.

"High-speed centrifugation" means centrifugation at about 8,500×g (±5% or ±10%) for about 10 minutes (±5% or ±10%), or the equivalent sedimentation protocol thereof.

"Clarifying," or clarification of a supernatant fraction means removing particulate matter (e.g., precipitates, bacteria) from a solution containing such particulate matter through the use of standard separation techniques, such as low- or high-speed centrifugation (as defined above) or filtration.

With respect to fractionation of the particular supernatant fractions, the phrase "less than about 3.5 kDa" as used herein refers to less than 3.5 kDa, or less than a molecular weight that varies by ±5% or ±10% therefrom. Similarly, the phrase "proteins or polypeptides of molecular weight of about 3.5 to about 30 kDa" as used herein refers to proteins or polypeptides in a molecular weight ranged from 3.5 kDa, or from a molecular weight that varies by ±5% or ±10% therefrom, to 30 kDa, or to a molecular weight that varies by ±5% or ±10% therefrom.

With respect to pH and ionic strength, the phrase "a pH value of about 7, or an ionic strength of about 0.85% w/v." as used herein refers to a pH of 7 or a pH that varies by ±5% or ±10% therefrom, and/or an ionic strength of 0.85% w/v, or an ionic strength that varies by ±5% or ±10% therefrom.

"Vaccine" is defined herein in its broad sense to refer to any type of biological agent, administrable for the purpose of priming, enabling or enhancing an immune response against in an animal inoculated with the vaccine.

Methods for Preparing Thymus Extracts:

Particular embodiments of the present invention (see working EXAMPLES 1-8) provide novel processes for preparing therapeutically useful extracts (Thyex-1-6A and -6B) of thymus tissue. In particular aspects, the inventive processes are readily distinguishable from other known processes for preparing thymus extracts (e.g., Goldstein & White, Contemp. Topics in Immunobiology, p. 339, 1973; Bergesi, et al., *Folia Allergol. Immunol. Clin.* 21:201, 1977; Hooper, et al., "The purification and properties of bovine thymosin," *Ann. NY Acad. Sci.* 249:125, 1975; U.S. Pat. No. 4,826,680, issued 2 May 1989, to Jaeger, Pharmaceutical Composition Containing Thymus Extract Fractions), and lack steps involving decalcite ($CaCO_3$) treatment, protease digestion, extraction with organic solvents (e.g., phenol, acetone or ethanol) or fractionation by column chromatography. Not only are the inventive compositions surprisingly effective in view of the teachings of the art, but the compositions produced in accordance with the instant processes are also further distinguished from those of the prior art by the molecular weight ranges of their protein elements.

The instant processes comprise steps to optimize protein compositions for therapeutic use of. For example, particular of the below-described process embodiments (Thyex-1-6A and -6B) are designed to provide therapeutic compositions, and include ammonium sulfate precipitation/fractionation and/or lyophilization steps, respectively, to facilitate optimal protein concentration and fractionation. The Thyex-3 process embodiment lacks an ammonium sulfate or lyophilization step, but provides for a sufficiently concentrated composition by reusing (and thereby augmenting) an initial tissue homogenization supernatant fraction as homogenization fluid to homogenize additional tissue. The resulting Thyex-3 composition is less refined relative to those of Thyex-1 and Thyex-2, but is nonetheless suitably concentrated and formulated for efficacious delivery. The Thyex 6A and Thyex 6B process embodiments described below are designed to provide therapeutic compositions suitable for delivery as a topical ointment or by injection or inhalation, and include ammonium sulfate precipitation/fractionation steps. Thyex 5 is prepared from a similar process but is less refined (less fractionated) than Thyex 6A or Thyex 6B and is optimally mixed with an amount of an extracted lyophilized herbal source composition, and administered orally in filled gelatin capsules. The Thyex 4 process embodiment lacks ammonium sulfate precipitation step but comprises lyophilization to provide for a sufficiently concentrated composition. The resulting Thyex 4 composition is less refined in relative to those of Thyex 5 or Thyex 6A or 6B, but is nonetheless suitably concentrated and formulated for efficacious oral deliver in both animals and humans.

Particular specific aspects provide a method for preparing a thymus extract composition, comprising: homogenizing thymus tissue with aqueous homogenization fluid to produce an aqueous thymus homogenate; removing tissue debris from the aqueous thymus homogenate to produce a primary supernatant; and heat denaturing and clarifying the primary supernatant to produce a clarified supernatant. In certain aspects, the method further comprises further clarifying of the clarified supernatant by high-speed centrifugation to produce a final clarified supernatant fraction. In certain embodiments, the method further comprises sterilizing the final clarified supernatant fraction to produce a sterile final clarified supernatant fraction. In particular aspects, sterilizing is achieved by passing the final clarified supernatant fraction through a membrane filter. In particular implementations, the initial ratio of thymus tissue to aqueous homogenization fluid is about 350 g wet weight of thymus tissue to about 0.7 L of homogenization fluid. In certain aspects, removing tissue debris from the aqueous thymus homogenate is achieved by a combination of low-speed centrifugation and crude filtration. In particular aspects, heat denaturing and clarifying of the primary supernatant is achieved by heat denaturation, followed by low-speed centrifugation and crude filtration to remove particulate matter. In certain implementations, the method further comprises lyophilization of the final clarified supernatant fraction.

Additional aspects provide a method for preparing a thymus extract composition, comprising: homogenizing thymus tissue with aqueous homogenization fluid to produce an aqueous thymus homogenate; removing tissue debris from the aqueous thymus homogenate to produce a primary supernatant; heat denaturing and clarifying the primary supernatant to produce an intermediate supernatant; and concentrating the intermediate supernatant to produce a concentrated intermediate fraction. In certain aspects, the method further comprises further clarifying of the concentrated intermediate fraction by high-speed centrifugation to produce a final clarified supernatant fraction. In particular embodiments, the method further comprises fractionating the final clarified supernatant fraction to remove molecules having a molecular weight less than about 3.5 kDa to produce a fractionated intermediate fraction. In certain aspects, the method further comprises fractionating the fractionated intermediate fraction, based on molecular weight, to obtain a fraction having proteins of about 3.5 to about 30 kDa. In particular implementations, the method further comprises adjusting at least one of the pH or ionic strength of the fraction having proteins of about 3.5 to about 30 kDa to a physiological or therapeutically compatible value, to produce a pH- or ionic strength-adjusted fraction. In certain aspects, adjusting at least one of the pH or ionic strength to a physiological or therapeutically compatible value is achieved by adding phosphate buffer or sodium chloride to produce a fraction having at least one of a pH value of about 7 or an ionic strength of about 0.85% w/v. In certain aspects, the method further comprises sterilizing the pH-, or ionic strength-adjusted fraction to produce a sterile pH-, or ionic strength-adjusted fraction. In particular embodiments, sterilizing is achieved by passing the fraction through a membrane filter. In certain aspects, the initial ratio of thymus tissue to aqueous homogenization fluid is about 350 g wet weight of thymus tissue to about 0.7 L of homogenization fluid. In particular embodiments, removing tissue debris from the aqueous thymus homogenate is achieved by a combination of low-speed centrifugation and crude filtration. In certain aspects, heat denaturing and clarifying of the secondary supernatant is achieved by heat denaturation, followed by low-speed centrifugation and crude filtration to remove particulate matter. In particular implementations, concentrating the intermediate supernatant involves concentrating and fractionating, and wherein the concentrating and fractionating is achieved by adding ammonium sulfate to the intermediate supernatant, followed by low-speed centrifugation and suspension of the resulting ammonium sulfate pellet in an aqueous solution. In some embodiments, fractionating the concentrated intermediate fraction to remove molecules having a molecular weight less than about 3.5 kDa is achieved by dialysis of the concentrated intermediate fraction, followed by high-speed centrifugation to remove particulate matter. In particular aspects, fractionating the fractionated intermediate fraction, based on molecular weight, is achieved by passing the fractionated intermediate fraction consecutively through a first and a second membrane filter having exclusion limits of about 100 and about 30 kDa, respectively, and collecting the filtrate. In certain aspects, the method further comprises lyophilization of the fraction having proteins of about 3.5 to about 30 kDa.

Particular specific aspects provide a process for preparing a thymus extract composition, comprising: homogenizing thymus tissue with aqueous homogenization fluid to produce an aqueous thymus homogenate; removing tissue debris from the aqueous thymus homogenate to produce a primary supernatant; concentrating the primary supernatant to produce a secondary supernatant; and denaturing and clarifying the secondary supernatant to produce a clarified supernatant. In certain embodiments, the method further comprises further clarifying of the clarified supernatant by high-speed centrifugation to produce a final clarified supernatant fraction. In particular embodiments, the method further comprises sterilizing the final clarified supernatant fraction to produce a sterile final clarified supernatant fraction. In certain implementations, sterilizing is achieved by passing the final clarified supernatant fraction through a membrane filter. In certain aspects, the initial ratio of thymus tissue to aqueous homogenization fluid is about 300 g wet weight, or about 340 ml wet volume, of thymus tissue to about 0.8 L of homogenization fluid. In certain aspects, removing tissue debris from the aqueous thymus homogenate is achieved by a combination of low-speed centrifugation and crude filtration. In particular embodiments, concentrating the primary supernatant is achieved by repeating (a) and (b) using the primary supernatant, in place of the aqueous homogenization fluid, for homogenizing additional thymus tissue. In certain aspects, denaturing and clarifying of the secondary supernatant is achieved by heat denaturation, followed by low-speed centrifugation and crude filtration to remove particulate matter.

Additional specific aspects provide a method for preparing a thymus extract composition, comprising: homogenizing thymus tissue with aqueous homogenization fluid to produce an aqueous thymus homogenate; removing tissue debris from the aqueous thymus homogenate to produce a primary supernatant; concentrating the primary supernatant to produce a secondary supernatant; denaturing and clarifying the secondary supernatant to produce an intermediate supernatant; concentrating the intermediate supernatant to produce a concentrated intermediate fraction; fractionating the concentrated intermediate fraction to remove molecules having a molecular weight less than about 3.5 kDa to produce a fractionated intermediate fraction; and fractionating the fractionated intermediate fraction, based on molecular weight, to obtain a fraction having proteins of about 3.5 to about 30 kDa. In certain embodiments, the method further comprises adjusting at least one of the pH or ionic strength of the fraction having proteins of about 3.5 to about 30 kDa to a physiological or therapeutically compatible value, to produce a pH- or ionic strength-adjusted fraction. In particular implementations, adjusting at least one of the pH or ionic strength to a physiological or therapeutically compatible value is achieved by adding phosphate buffer or sodium chloride to produce a fraction having at least one of a pH value of about 7 or an ionic strength of about 0.85% w/v. In some aspects, the method further comprises sterilizing the pH-, or ionic strength-adjusted fraction to produce a sterile pH-, or ionic strength-adjusted fraction. In particular embodiments, sterilizing is achieved by passing the fraction through a membrane filter. In certain aspects, the initial ratio of thymus tissue to aqueous homogenization fluid is about 350 g wet weight of thymus tissue to about 0.7 L of homogenization fluid. In certain embodiments, removing tissue debris from the aqueous thymus homogenate is achieved by a combination of low-speed centrifugation and crude filtration. In certain aspects, concentrating the primary supernatant is achieved by repeating (a) and (b) using the primary supernatant, in place of the aqueous homogenization fluid, for homogenizing additional thymus tissue. In particular implementations, denaturing and clarifying of the secondary supernatant is achieved by heat denaturation, followed by low-speed centrifugation and crude filtration to remove particulate matter. In particular aspects, the intermediate supernatant is concentrated, wherein concentrating is achieved by lyophilizing the intermediate supernatant either to complete dryness followed by aqueous resuspension to about 500 ml/13.6 kg (30 lbs.) original wet tissue, or to a volume of about 10% of its original volume. In particular aspects, concentrating the intermediate supernatant involves concentrating and fractionating, and wherein the concentrating and fractionating is achieved by adding ammonium sulfate to the intermediate supernatant, followed by low-speed centrifugation and suspension of the resulting ammonium sulfate pellet in an aqueous solution. In certain embodiments, fractionating the concentrated intermediate fraction to remove molecules having a molecular weight less than about 3.5 kDa is achieved by dialysis of the concentrated intermediate fraction, followed by high-speed centrifugation to remove particulate matter. In particular aspects, fractionating the fractionated intermediate fraction, based on molecular weight, is achieved by passing the fractionated intermediate fraction consecutively through a first and a second membrane filter having exclusion limits of about 100 and about 30 kDa, respectively, and collecting the filtrate.

Additional aspects provide a pharmaceutical composition, comprising a thymus extract composition produced in accordance with one or more of the processes disclosed herein.

Methods of Treating:

The term "treating" refers to, and includes, reversing, alleviating, inhibiting the progress of, or preventing a disease, disorder, or condition, or one or more symptoms thereof; and "treatment" and "therapeutically" refer to the act of treating, as defined herein.

A "therapeutically effective amount" is any amount of any of the compounds utilized in the course of practicing the invention provided herein that is sufficient to reverse, alleviate, inhibit the progress of, or prevent a disease, disorder, or condition, or one or more symptoms thereof.

According to particular aspects the methods comprise administration of a composition comprising at least one of Thyex-1-6A and -6B, as defined herein, and formulated with colostrum, including optionally in combination with (e.g., adjunctive therapy), for example, with administration of an anti-parasitic agent, anti-viral agent, anti-bacterial agent, anti-fungal agent, and/or with a macrophage stimulating agent.

According to particular aspects, a polysaccharide is used as preferred macrophage stimulating agent. In preferred aspects, the macrophage stimulating agent comprises a beta glucan. In particular embodiments, the beta glucan comprises at least one linkage selected from the group consisting of beta: 1,3; 1,4; and 1,6 glucan linkages. Preferably, the linkage is that of beta 1,3 glucan.

According to particular aspects the inventive Thyex compositions are used in adjunctive therapies with extracts of at least one of: *Paresis crepe* (aka cauliflower mushroom or hanabaritake) preparations comprising beta 1-3 glucan; *Lentinula edodes* (shitake; e.g., alkaline digest according to the procedure reported by Ohno et al. (Biol. Phar. Bull. 23:866-872, 2000), comprises beta 1-3 glucan and chitin; *Astralagas membranaceus; Scutellaria baicalensis; Lilium longiforum* (aka Easter lily); and *Houttuynia cordata* extracts.

Additional aspects provide a pharmaceutical composition, comprising a thymus extract composition produced in accordance with one or more of the processes disclosed herein.

Combination therapies. Combination therapies are also encompassed by aspects of the present invention. For example, the inventive methods may further comprise administration of a therapeutically effective amount of one or more anti-microbial agents, such as anti-parasitic, anti-viral agents, anti-bacterial agents, anti-fungal agents. Examples of anti-viral agents include but are not limited to: combivir, boceprevir, abacavir, docosanol, aciclovir, didanosine, cidofovir, acyclovir, delavirdine, adefovir, amantadine, amprenavir, arbidol, darunavir atazanavir, atripla, zanamivir, and oseltamivir. Examples of anti-bacterial agents include but are not limited to: metronidazole, tinidazole, co-trimoxazole, cephamandole, ketoconazole, latamoxef, cefoperazone, amoxicillin, cefmenoxime, furazolidone, doxycycline and erythromycin. Examples of antifunal agents include but are not limited to: imidazoles, (e.g., miconazole, ketoconazole, clotrimazole, econazole, bifonazole, butoconazole, fenticonazole, isoconazole, oxiconazole, sertaconazole, sulconazole, and tioconazole), triazoles (e.g., fluconazole, itraconazole, isavuconazole, ravuconazole, posaconazole, voriconazole, and terconazole), thiazoles (e.g., abafungin), allylamines (e.g., terbinafine, amorolfine, naftifine, and butenafine), and echinocandins (e.g., anidulafungin, caspofungin, and micafungin).

Methods for Treatment of Stomatitis (e.g., Gingivostomatitis) Using the Inventive Thyex Compositions and Combinations Thereof:

According to additional aspects (see working EXAMPLE 9 below), Applicant's Thyex compositions have substantial utility for treating stomatitis (e.g., gingivostomatitis). A thymic extract, Kyosenex® was used in management of a protracted case of feline gingivostomatitis. The patient responded dramatically, especially in the caudal portion of the oral cavity. The condition recurred upon stopping therapy and improved again on reinstituting the agent. Quality of life was greatly improved.

Preferred embodiments relates to a method for treating stomatitis (e.g., gingivostomatitis), comprising administering to a mammalian subject in need thereof an effective amount of a thymus extract composition produced in accordance with the methods recited herein, wherein effects of stomatitis (e.g., gingivostomatitis related inflammation) alleviated. In further preferred embodiments, the mammalian subject in need of treatment includes but is not limited to canine, feline, bovine, porcine, equine, ovine, and other large animals. In preferred embodiments, the method for treating stomatitis (e.g., gingivostomatitis) includes veterinary applications (e.g., canine and feline).

Methods for Treatment of Demodectic Mange Using the Inventive Thyex Compositions and Combinations Thereof:

According to additional aspects (see working EXAMPLE 10 below), Applicant's Thyex compositions have substantial utility for treating demodectic mange. A thymic extract, Kyosenex® was used in management of a protracted case of canine demodectic mange. The patient responded dramatically. At one-year post treatment, there has been no recurrence of the condition.

In working EXAMPLE 11, an additional five dogs having previously untreatable demodectic mange were treated with Kyosenex®. A favorable response was seen in 3/5 animals treated (60%).

Methods for Treatment of Itching Using the Inventive Thyex Compositions and Combinations Thereof with Colostrum Formulations:

Additional combinations of the thymus extracts with colostrum (e.g., bovine colostrum) are disclosed herein (see working EXAMPLE 13), and provide for reducing itching as described herein.

Compositions:

Additional embodiments provide compositions produced in accordance with said processes. The Thyex-1, -2, -3, -4, -5, -6A, and -6B composition embodiments are produced in accordance with the corresponding Thyex-1-6A and -6B processes (Working EXAMPLES 1-8).

Methods of Treatment:

Further embodiments provide methods for treatment of demodectic mange and stomatitis (e.g., gingivostomatitis) comprising: utilizing thymus extract compositions alone, or in combination with at least one other antimicrobial (anti-parasitic, anti-bacterial, anti-fungal, anti-viral) agent and/or at least one homeopathic agent and/or a macrophage stimulating agent.

Treatment with Thyex-1-6A and 6B compositions, with and without at least one other antimicrobial (antibacterial, antifungal, antiviral) agent and/or at least one a macrophage stimulating agent.

Further embodiments provide methods for treatment of itching comprising: utilizing thymus extract compositions in combination with colostrum (e.g., bovine colostrum), and optionally in further combination with at least one other antimicrobial (anti-parasitic, anti-bacterial, anti-fungal, anti-viral) agent and/or at least one homeopathic agent and/or a macrophage stimulating agent.

Treatment with Thyex-1-6A and 6B compositions, with and without at least one other antimicrobial (antibacterial, antifungal, antiviral) agent and/or at least one a macrophage stimulating agent.

Thyex-1-3 processes. EXAMPLES 1-3 provide exemplary process embodiments used for preparing Thyex-1-3, produced in accordance therewith suitable for oral delivery. Alternatively, Thyex-1-3 are lyophilized, stored at ambient temperature and reconstituted with sterile water prior to use.

Thyex-4 process. Steps (1)-(11) of EXAMPLE 4 comprise a process embodiment for producing Thyex-4 (step (12) relates to storage), suitable for oral delivery. Alternatively, Thyex-4 is lyophilized, stored at ambient temperature and reconstituted with sterile water prior to use.

Thyex-5 process. Steps (1)-(13) EXAMPLE 5 comprise a process embodiment for producing Thyex-5 (step (14) relates to storage), suitable for oral delivery. Alternatively, Thyex-5 is lyophilized, stored at ambient temperature and reconstituted with sterile water prior to use.

Thyex-6A process. EXAMPLE 6 provides an exemplary process embodiment used for preparing Thyex-6A produced in accordance therewith suitable for oral delivery, or delivery as a topical ointment or by injection or inhalation. Alternatively, Thyex-6A is lyophilized, stored at ambient temperature and reconstituted with sterile water prior to use.

Thyex-6B process. EXAMPLE 7 provides an exemplary process embodiment used for preparing Thyex-6B produced in accordance therewith suitable for oral delivery, or delivery as a topical ointment or by injection or inhalation. Alternatively, Thyex-6B was lyophilized, stored at ambient temperature and reconstituted with sterile water prior to use.

Dose Determinations

A therapeutically effective dose of a composition of the present invention refers to that amount of the composition sufficient to prevent or inhibit the effects of the treated condition, or to that amount sufficient to enhance the efficacy of adjunctive regimens. This amount may vary somewhat among subjects, but are nonetheless reasonably determined by one of ordinary skill within the art in view of the many art-recognized symptoms associated with the treated conditions.

Therapeutically effective doses of the disclosed compositions are administered alone or in combination with other therapeutic agents, such as macrophage stimulating agents, anti-microbial agents (e.g., antiviral, antifungal or antibacterial agents), or are administered as adjunctive therapy in combination with administration of other treatment regimens.

In particular aspects, as in the Examples herein, the Thyex compositions are standardized at a protein concentration about 2 mg/ml. Lyophilized compositions may be suspended, for example, using physiological saline with sodium chloride of 0.85-0.9%. Preferably, the daily dose range for Thyex administration by injection is from about 0.05 mg/kg to about 1 mg/kg. More preferably, the dose range for Thyex administration by injection is from about 0.05 mg/kg to about 0.5 mg/kg. Even more preferably, the dose range for Thyex administration by injection is from about 0.1 mg/kg to about 0.4 mg/kg. Most preferably, the dose range for Thyex administration by injection is from about 0.2 mg/kg to about 0.3 mg/kg.

In particular aspects, the daily dose range for Thyex oral administration is from about 1 mg/kg to about 20 mg/kg. More preferably, the dose range for Thyex oral administration is from about 1 mg/kg to about 10 mg/kg. Even more preferably, the dose range for Thyex oral administration is from about 3 mg/kg to about 9 mg/kg. Most preferably, the dose range for Thyex oral administration is from about 5 mg/kg to about 8 mg/kg.

In particular aspects, the daily dose range for adjunctive administration of beta glucan can be determined by routine optimization by one of ordinary skill in the art. In particular aspects, the daily dose range for adjunctive administration of the polysaccharide extract (e.g., consisting of about 70% beta 1-3 glucan and 30% tissue proteins) will be about 300 to about 500 mg per day for a typical patient (e.g., or about 0.5 mg/kg to 15 mg/kg). In particular embodiments, using more highly purified polysaccharide fractions (e.g., void of protein; e.g., extracted by the method of Ohno, et al. (*Biol Pharm Bul,* 23, p. 866, 2000), the daily dose will be about 300 mg per day (e.g., or about 0.5 mg/kg to 2.0 mg/kg) for a typical patient.

Antibiotic dosages were those of the label, according to the particular antibiotic used.

Doses of antifungal, antiviral, antiparasitic (e.g., mites) are according to those of the label, according to the particular agent used. For example, in dogs, typical doses for ivermectin are: 6 ug/kg for heartworm prevention; 300 ug/kg for treatment of sarcoptic mange; and 400-600 ug/kg for treatment of demodectic mange.

Dipping—Paramite dip (a discontinued organophosphate), and Lime-Sulfur dips were mainstays of treatment for *Sarcoptes,* but of very limited value in Demodecosis.

Goodwinol ointment—used for many decades, since approximately 10% of localized demodicosis cases will progress to generalized demodicosis, often accompanied by lymphadenopathy.

Ivermectin-broad spectrum, inexpensive, parasiticide. It must be used with caution in dogs with the MDR gene, such as sight hounds and herding breeds. Ivermectin injected or orally 0.05-3 mg/kg, depending on toleration. Success can be achieved giving ivermectin 2-3 times weekly, though the literature suggests daily dosing.

Moxidectin (Advantage Multi®) can be used to treat demodicosis and is often effective if used weekly.

Amitraz (Mitaban) Dip is an old therapy, with best efficacy at double strength and applied weekly. It can be quite toxic, particularly in small dogs. Preventic (amitraz) collars have had some success, but they must be changed often (about every 4 weeks).

Doramectin injections or orally 0.6 mg/kg, every 1-2 weeks, or milbemycin (Interceptor) 1-2 mg/kg every 2 weeks.

Milbemycin oxime (Interceptor) can be an effective, expensive approach to generalized demodicosis (0.52 to 3.8 mg/kg of body weight, q 24 hr). May be used in dogs with genetic sensitivity to Ivermectin (herding breeds, primarily, carrying the MDR gene). Some dogs require concurrent dipping.

Colostrum. As will be appreciated by one of ordinary skill in the art, the dosage administered will vary, depending upon the size, needs and responsiveness of the subject. For example, while 66.6 ug of Kyosenex®/ml colostrum is typical, less Kyosenex®/ml colostrum can be used. For example, 33.3 ug Kyosenex®/ml colostrum can be used, or 15 ug Kyosenex®/ml colostrum can be used. Generally, the amount of Kyosenex®/ml colostrum can vary between 5 to 100 ug of Kyosenex®/ml colostrum, more preferably between 10 to 80 ug of Kyosenex®/ml colostrum, even more preferably between 20 to 80 ug of Kyosenex®/ml colostrum, and most preferably between 30 to 70 ug of Kyosenex®/ml colostrum is used. Optionally, preservatives (e.g., methyl paraben and/or propyl paraben) can be included.

Formulations and Use

In particular preferred aspects, Thyex-1-6A and -6B in combination with, or formulated with colostrum, have substantial utility in methods for treatment of itching associated with various mammalian conditions including, but not limited to itching relating to allergy, demodectic mange and stomatitis (e.g., gingivostomatitis), comprising administration (e.g., oral) of said compositions.

In particular preferred aspects, Thyex-1-6A and -6B have substantial utility in methods for treatment of various Human and mammalian conditions including, but not limited to demodectic mange and stomatitis (e.g., gingivostomatitis), comprising administration of said compositions.

For administration by injection, the Thyex compositions and colostrum formulations thereof of the present invention are preferably formulated in aqueous solutions with physiologically compatible buffered saline (e.g., phosphate buffered standard physiological saline; 0.85% NaCl).

For oral administration, the pharmaceutical Thyex compositions and colostrum formulations thereof of the present invention may take the form of, for example, liquids, gels, syrups, slurries, and the like, prepared by conventional means with pharmaceutically acceptable excipients such as: binding agents (e.g., pre-gelatinized maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP)); fillers (e.g., lactose, sucrose, mannitol, or sorbitol, microcrystalline cellulose or calcium hydrogen phosphate); lubricants (e.g., magnesium stearate, talc or silica); disintegrants (e.g., potato starch, sodium starch glycolate, cross-linked polyvinyl pyrrolidone, agar, or alginic acid or a salt thereof such as sodium alginate); or wetting agents (e.g., sodium lauryl sulfate). Such liquid preparations are prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Additional oral administration can be in the form of an effervescent tablet. Effervescent formulations are known in the art for various active ingredients and vitamins. These effervescent formulations generally include an agent that is capable of releasing $CO_2$, and an agent which induces the release of $CO_2$. Suitable agents capable of releasing $CO_2$ which are used include alkali metal carbonates or alkali metal bicarbonates, such as sodium carbonate and sodium bicarbonate. Alkaline earth metal carbonate formulations are mainly contained in mineral preparations. Suitable agents for inducing $CO_2$ release include edible organic acids, or their acidic salts, which are present in solid form and which can be formulated with the active ingredient and the other auxiliaries to provide granules or tablets, without premature evolution of $CO_2$. The active ingredients are either present in the effervescent formulation as readily soluble compounds, or they are solubilized by salt formation during the dissolution process.

For administration by inhalation, the Thyex compositions and colostrum formulations thereof for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide, or other suitable gas. In the case of a pressurized aerosol, the dosage unit may be determined by providing a valve to deliver a metered amount.

The Thyex compositions and colostrum formulations thereof of the present invention may be formulated for parenteral administration by injection by bolus injection or continuous infusion. Formulations for injection may be presented in unit dosage form in ampoules or in multi-dose containers, with optionally, with an added preservative.

Vaccines are either those commercially available, or those prepared according to art-recognized methods, and are of various forms, including conventional forms such as aqueous dispersions, oil emulsions, liposome compositions, lyophilized forms, etc. Vaccine compositions and vaccination regimens may comprise different adjuvants, emulsifiers, stabilizers, etc. Vaccines are administered by different routes, including but not limited to parenteral, intramuscular, intranasal, intratracheal, subcutaneous, cutaneous, percutaneous, or intracutaneous routes, and combinations thereof.

Vaccines may be prepared, inter alia, as aqueous solutions, syrups, elixers, or tinctures, and the liquid formulations may include suspensions and/or emulsions.

Thyex-4 may be lyophilized and dispensed in "00" size gelatin capsules: Oral. Approximately 40% thymic polypeptides.

Thyex-5. In particular aspects, Thyex-5 (e.g., lyophilized; approximately 80% thymic polypeptides) is mixed with other extracts (e.g., extracts containing polysaccharides such as beta 1-3 glucan). The mixtures, for example, can be dispensed in "00" gelatin capsules, or alternatively, for example, in size "3" capsule if not mixed with other extracts.

Thyex-6A. In particular aspects, Thyex-6A (e.g., sterile liquid extract) can be used to generate aerosols (e.g., for treating pneumonia or emphysema). Alternatively, for example, ointments can be used when Thyex-6A is mixed with water-soluble ointment base.

Thyex-6B. In particular aspects, Thyex-6BA (e.g., sterile liquid buffered, and saline adjusted for injection; at least 99% pure) is used for veterinary and human uses.

Uses for the Thyex compositions include, but are not limited to veterinary uses including, but not limited to treating demodectic mange and stomatitis (e.g., gingivostomatitis).

In addition to the ingredients specifically mentioned above, the formulations of the present invention may include other agents known to those skilled in the art, having regard for the type of formulation in issue. For example, formulations suitable for oral administration may include flavoring agents and formulations suitable for intranasal administration may include perfumes.

The therapeutic compositions and formulations of the invention can be administered by any conventional method available for use in conjunction with pharmaceutical drugs, either as individual therapeutic agents or in a combination of therapeutic agents.

The dosage administered will, of course, vary depending upon known factors, such as the pharmacodynamic characteristics of the particular agent and its mode and route of administration; the age, health and weight of the recipient; the nature and extent of the symptoms; the kind of concurrent treatment; the frequency of treatment; and the effect desired.

The injection-use formulations can be presented in unit-dose or multi-dose sealed containers, such as ampules and vials, and can be stored in a freeze-dried (lyophilized) condition requiring only the addition of the sterile liquid excipient immediately prior to use. Extemporaneous injection solutions and suspensions can be prepared from sterile powders, granules, and tablets. The requirements for effective pharmaceutical carriers for injectable compositions are well known to those of ordinary skill in the art. See, for example, Pharmaceutics and Pharmacy Practice, J. B. Lippincott Co., Philadelphia, Pa., Banker and Chalmers, Eds., 238-250 (1982) and ASHP Handbook on Injectable Drugs, Toissel, 4th ed., pp. 622-630 (1986).

Formulations suitable for topical administration include lozenges of the compositions and optionally, an additional therapeutic and a flavor, usually sucrose and acacia or tragacanth; pastilles comprising a gas-enriched fluid and optional additional therapeutic agent in an inert base, such as gelatin and glycerin, or sucrose and acacia; and mouth washes or oral rinses comprising a gas-enriched fluid and optional additional therapeutic agent in a suitable liquid carrier; as well as creams, emulsions, gels, and the like.

Additionally, formulations suitable for rectal administration may be presented as suppositories by mixing with a variety of bases such as emulsifying bases or water-soluble bases. Suitable pharmaceutical carriers are described in Remington's Pharmaceutical Sciences, Mack Publishing Company, a standard reference text in this field.

The dose administered to a subject, especially an animal, particularly a human, in the context of the present invention should be sufficient to effect a therapeutic response in the animal over a reasonable time frame. One skilled in the art will recognize that dosage will depend upon a variety of factors including the condition of the animal, the body weight of the animal, as well as the condition being treated. A suitable dose is that which will result in a concentration of the therapeutic composition in a subject that is known to affect the desired response.

The size of the dose also will be determined by the route, timing and frequency of administration as well as the existence, nature, and extent of any adverse side effects that might accompany the administration of the therapeutic composition and the desired physiological effect.

Most suitable means of administration for a particular subject will depend on the nature and severity of the disease or condition being treated or the nature of the therapy being used, as well as the nature of the therapeutic composition or additional therapeutic agent. In certain embodiments, oral or topical administration is preferred.

Formulations suitable for oral administration may be provided as discrete units, such as tablets, capsules, cachets, syrups, elixirs, chewing gum, "lollipop" formulations, microemulsions, solutions, suspensions, lozenges, or gel-coated ampules, each containing a predetermined amount of the active compound; as powders or granules; as solutions or suspensions in aqueous or non-aqueous liquids; or as oil-in-water or water-in-oil emulsions.

In addition to the ingredients specifically mentioned above, the formulations of the present invention may include other agents known to those skilled in the art, having regard for the type of formulation in issue. For example, formulations suitable for oral administration may include flavoring agents and formulations suitable for intranasal administration may include perfumes.

The therapeutic compositions of the invention can be administered by any conventional method available for use in conjunction with pharmaceutical drugs, either as individual therapeutic agents or in a combination of therapeutic agents.

EXAMPLE 1

Preparation of Thymus Extracts Thyex-1

This example provides an exemplary process embodiment used for preparing thymus extracts, and compositions ("Thyex-1") produced in accordance therewith:
Thyex-1:
Thyex-1 process. The following steps (1)-(16) comprise a process embodiment for producing Thyex-1 (step (17) relates to storage) suitable for oral delivery:

(1) Homogenization of thymus tissue. Fresh "prime" (i.e., not fibrous or whitish in appearance) porcine or bovine thymus glands were frozen (e.g., overnight). The frozen glands were rinsed briefly in clean water and "dressed" by removal of any associated fibrous or connective tissue, fatty tissue, or lymph node tissue. The prime washed, dressed thymus glands were cut into small pieces (e.g., about 2" cubes using a sharp knife), and homogenized through the use of a food processor or other grinding apparatus (e.g., a meat grinder). For homogenization, a volume of approximately 700 ml of 0.2% NaCl solution (in distilled water) was blended with approximately 350 g wet weight (about 400 ml wet volume) of cut-up thymus tissue in a standard size blender for at least one minute to produce a thymus homogenate;

(2) Low-speed Centrifugation. The "thymus homogenate" of step (1) was centrifuged at about 3,500×G for 10 minutes at ambient temperature to produce a pellet and a supernatant fraction;

(3) Crude filtration. The resulting "supernatant fraction" of step (2) (after removal of any packed low density debris floating on its surface) was decanted from the centrifugation pellet and gravity filtered through one or more layers of standard cheese cloth to produce a primary filtered supernatant;

(4) Production of a "secondary filtered supernatant." Steps (1)-(3) were repeated with another 350 g wet weight (about 400 ml wet volume) of prime washed, dressed, cut-up thymus glands, except that the "primary filtered supernatant" of step (3) was used in place of the 700 ml of 0.2% NaCl solution of step (1). This substitution allowed for the production of a more concentrated (relative to the "primary filtered supernatant") secondary filtered supernatant;

(5) Heat denaturation. The "secondary filtered supernatant" of step (4) was heated to a temperature of about 75-80° C. by exposing the container thereof to a uniform heat source, such as a constant temperature water bath set at about 100° C., or a double boiler containing water at about 100° C. During said heating, the "secondary filtered supernatant" was frequently agitated or stirred until it reached about 75-80° C. to produce a heat-denatured secondary filtered supernatant;

(6) Low-speed Centrifugation. The "heat-denatured secondary filtered supernatant" of step (5) was centrifuged at 3,500×g for 5 minutes at ambient temperature to produce a pellet and a heat-denatured supernatant fraction;

(7) Production of a "heat-denatured filtered supernatant." The "heat-denatured supernatant fraction" of step (6) was decanted from the centrifugation pellets and gravity filtered through one or more layers of standard cheese cloth to produce a filtered, heat-denatured supernatant fraction (hereinafter the "intermediate supernatant" fraction) that was still slightly warm from the heat denaturation of step (5);

(8) Ammonium sulfate precipitation. About 650 gm of ammonium sulfate was added to 1 L of the warm "intermediate supernatant" of step (7). The solution was stirred until all the ammonium sulfate was dissolved, and then allowed to stand for about 1 hour at ambient temperature to produce a salted intermediate supernatant fraction;

(9) Low-speed centrifugation. The "salted intermediate supernatant" of step (8) was divided between two, 1 L centrifuge bottles and centrifuged at 3,500×g for 10 minutes at ambient temperature to produce ammonium sulfate pellets, and supernatant fractions;

(10) Suspension of ammonium sulfate pellet fraction. The "ammonium sulfate supernatants" from step (9) were decanted from the centrifugation tubes and discarded, and excess salt solution was carefully wiped from the inside tube walls. The two ammonium sulfate pellets of step (9) (i.e., corresponding to each 1-L centrifuge bottle) were then suspended and dissolved by gentle mixing with about 50 ml of 0.01 to 0.05 M phosphate buffer (about pH 7) for each pellet (alternatively, the pellets were suspended with distilled water). The suspensions were allowed to stand for about 1 hour at ambient temperature with brief agitation about every 15 minutes (to facilitate complete dissolution of the pellets) to provide an ammonium sulfate fraction. Note that dissolution of any remaining ammonium sulfate pellet can be affected by the step-wise addition of small amounts of distilled water (e.g., 5 ml aliquots), followed by agitation until the pellet is completely dissolved;

(11) Dialysis. The "ammonium sulfate" fraction of step (10) was transferred to clean dialysis tubing (e.g., Spectrapor 3.5 kDa molecular weight cut-off size), and dialyzed with stirring (e.g., by means of a magnetically-driven stir bar in the dialysis chamber) for 3 days against an excess of distilled water at about 4° C. to produce a dialyzed ammonium sulfate fraction. The distilled water was changed every 12 hours. Increasing hydrostatic pressure within the dialysis tubing was periodically relieved by removing some of the dialysate and transferring it to additional dialysis tubes;

(12) High-speed centrifugation. The "dialyzed ammonium sulfate fraction" of step (11) was centrifuged at 8,500×g for 10 minutes at ambient temperature to produce a pellet and dialyzed ammonium sulfate supernatant fraction;

(13) First exclusion-membrane filtration. The "dialyzed ammonium sulfate supernatant fraction" of step (12) was passed under nitrogen pressure at about 40-50 psi. through a 100 kDa exclusion limit membrane filter (Amicon) at 4° C. (alternatively, ambient temperature will suffice) to produce a 3.5 kDa to 100 kDa filtrate;

(14) Second exclusion-membrane filtration. The "3.5 kDa to 100 kDa filtrate" of step (13) was passed under nitrogen pressure at 40 to 50 psi. (275.8 to 344.75 Kpa, in metric units) through a 30 kDa exclusion limit membrane filter (Amicon) to produce a 3.5 kDa to 30 kDa filtrate;

(15) Adjustment of pH and ionic strength. About 5 ml of 1 M phosphate buffer (about pH 7) per liter was added to the "3.5 kDa to 30 kDa filtrate" of step (14). Solid NaCl was then added to 0.85% (weight to volume) to produce a pH- and ionic strength-adjusted 30 kDa filtrate, Thyex-1;

(16) Filter sterilization. The "Thyex-1" of step (15) was filter sterilized by passage through a 0.2 micron membrane filter to produce sterile Thyex-1, suitable for oral delivery; and

(17) Storage. Thyex-1, produced in accordance with steps (1)-(16) of the Thyex-1 process, was typically stored frozen (e.g., −5° C. to −20° C.) in sterilized containers, and thawed just prior to use. According to particular aspects, the therapeutic activity of Thyex-1 was found to be stable to repeated freezing and thawing. Alternatively, Thyex-1 was lyophilized, stored at ambient temperature and reconstituted with sterile water prior to use.

According to particular aspects, one or more of the above steps are optional.

EXAMPLE 2

Preparation of Thymus Extracts Thyex-2

This example provides an exemplary process embodiment used for preparing thymus extracts, and compositions ("Thyex-2") produced in accordance therewith suitable for oral delivery:
Thyex-2:

Thyex-2 process. The following steps (1)-(8) comprise a process embodiment for producing Thyex-2 (step (9) relates to storage):

(1) Production of "intermediate supernatant." Steps (1)-(7) of the above-identified Thyex-1 process for the preparation of "intermediate supernatant" were followed (except that steps (1)-(3) were not repeated as in the Thyex-1 process) to produce an "intermediate supernatant" fraction;

(2) High-speed centrifugation. The "intermediate supernatant" fraction of step (1) was cleared (i.e., to remove potential pathogens) by centrifugation at 8,500×g for 10 minutes at ambient temperature to produce a pellet and a cleared intermediate supernatant fraction;

(3) Lyophilization. The "cleared intermediate supernatant" fraction of step (2) was lyophilized (i.e., freeze dried) either to complete dryness to produce a dried, cleared intermediate supernatant fraction, or until its volume was reduced by 90% to produce a lyophilized, cleared intermediate supernatant fraction;

(4) Dialysis. The "lyophilized, cleared intermediate supernatant," or the alternative completely "dried" fraction (suspended in 500 ml distilled water per 13.6 kg (30 lbs.) wet weight of thymus glands processed) of step (3) was dialyzed according to step (11) of the above-identified Thyex-1 process to produce a dialyzed, lyophilized intermediate supernatant fraction;

(5) High-speed centrifugation. The "dialyzed, lyophilized intermediate supernatant" of step (4) was centrifuged at 8,500×g for 10 minutes at ambient temperature to produce a pellet, and a cleared, dialyzed, lyophilized intermediate supernatant fraction;

(6) Exclusion-Membrane filtration. The "cleared dialyzed, lyophilized intermediate supernatant" of step (5) was passed consecutively under nitrogen pressure (40-50 p.s.i.) through 100 kDa and 30 kDa exclusion limit membrane filters (Amicon), according to steps (13) and (14) of the above-identified Thyex-1 process to produce a 3.5 kDa to 30 kDa filtrate. The protein concentration of the "30 kDa filtrate" was measured, and optionally diluted (typically, to about 2 mg/0.25 ml (lesser or greater dilutions were also made as desired);

(7) Adjustment of pH and ionic strength. The pH and ionic strength of the "3.5 kDa to 30 kDa filtrate" or the optionally diluted "3.5 kDa to 30 kDa filtrate" of step (6) was adjusted according to step (15) of the above-identified Thyex-1 process to produce a pH- and ionic strength-adjusted 3.5 kDa to 30 kDa filtrate, Thyex-2;

(8) Filter sterilization. The "Thyex-2" of step (7) was filter sterilized according to step (16) of the above-identified Thyex-1 process to produce sterile Thyex-2, suitable for oral delivery; and (9) Storage. Thyex-2, produced in accordance with steps (1)-(8) of the Thyex-2 process was typically stored frozen (e.g., −5° C. to −20° C.) in sterilized containers, and thawed just prior to use. According to particular aspects, the therapeutic activity of Thyex-2 was found to be stable to repeated freezing and thawing. Alternatively, Thyex-2 was lyophilized, stored at ambient temperature and reconstituted with sterile water prior to use.

According to particular aspects, one or more of the above steps are optional.

EXAMPLE 3

Preparation of Thymus Extracts Thyex-3

This example provides an exemplary process embodiment used for preparing thymus extracts, and compositions ("Thyex-3") produced in accordance therewith suitable for oral delivery:
Thyex-3:

Thyex-3 process. The following steps (1)-(10) comprise a process embodiment for producing Thyex-3 (step (11) relates to storage), suitable for oral delivery:

(1) Homogenization of thymus tissue. Fresh "prime" (i.e., not fibrous or whitish in appearance) porcine or bovine thymus glands were frozen (e.g., overnight). The frozen glands were rinsed briefly in clean water and "dressed" by removal of any associated fibrous or connective tissue, fatty tissue, or lymph node tissue. The prime washed, dressed thymus glands were cut into small pieces (e.g., about 2" cubes using a sharp knife), and homogenized through the use of a food processor or other grinding apparatus (e.g., a meat grinder). For homogenization, a volume of approximately 800 ml of 0.2% NaCl solution (in distilled water) was blended with approximately 300 g wet weight (about 340 ml wet tissue volume) of cut-up thymus tissue in a standard size blender for at least one minute to produce a thymus homogenate;

(2) Low-speed Centrifugation. The "thymus homogenate" of step (1) was centrifuged at about 3,500 rpm for 10 minutes at ambient temperature to produce a pellet and a supernatant fraction;

(3) Crude filtration. The resulting "supernatant fraction" of step (2) (after removal of any packed low density debris floating on its surface) was decanted from the centrifugation pellet and gravity filtered through one or more layers of standard cheese cloth to produce a primary filtered supernatant;

(4) Production of a "secondary filtered supernatant." Steps (1)-(3) were repeated with another 175 g wet weight (200 ml wet tissue volume) of prime washed, dressed, cut-up thymus glands, except that the "primary filtered supernatant" of step (3) was used in place of the 800 ml of 0.2% NaCl solution of step (1). This substitution allowed for the production of a more concentrated (relative to the "primary filtered supernatant") secondary filtered supernatant;

(5) Production of a "tertiary filtered supernatant." Steps (1)-(3) were repeated with another 200 ml (wet volume) of prime washed, dressed, cut-up thymus glands, except that the "secondary filtered supernatant" from step (4) was used in place of the 800 ml of 0.2% NaCl solution of step (1). This substitution allowed for the production of a more concentrated (relative to the "primary" and "secondary filtered supernatants") tertiary filtered supernatant;

(6) Heat denaturation. The "tertiary filtered supernatant" from step (5) was heated to a temperature of about 75-80° C. by exposing the container thereof to a uniform heat source such as a constant-temperature water bath set at about 100° C. or a double boiler containing water at about 100° C. During heating, the "tertiary filtered supernatant" was frequently agitated or stirred until it reached about 75-80° C. to produce a heat-denatured tertiary filtered supernatant fraction;

(7) Low-speed Centrifugation. The "heat-denatured tertiary filtered supernatant" fraction of step (6) was centrifuged at 3,500 rpm for 5 minutes at ambient temperature to produce a pellet and a heat-denatured supernatant fraction;

(8) Production of a "heat-denatured filtered supernatant." The "heat-denatured supernatant fraction" of step (7) was decanted from the centrifugation pellets and gravity filtered through one or more layers of standard cheese cloth to produce a filtered, heat-denatured supernatant fraction that was still slightly warm from the heat denaturation of step (6);

(9) High-speed centrifugation. The "filtered, heat-denatured supernatant" fraction of step (8) was centrifuged at about 8,500×g for 5 minutes at ambient temperature to produce a pellet, and a high-speed supernatant fraction, Thyex-3;

(10) Filter sterilization. The "Thyex-3" fraction of step (9) was filter sterilized according to step (16) of the above-identified Thyex-1 process to produce sterile Thyex-3, suitable for oral delivery; and

(11) Storage. Thyex-3, produced in accordance with steps (1)-(10) of the Thyex-3 process was typically stored frozen (e.g., −5 to −20° C.) in sterilized containers, and thawed just prior to use. According to particular aspects, the therapeutic activity of Thyex-3 was found to be stable to repeated freezing and thawing. Alternatively, Thyex-3 was lyophilized, stored at ambient temperature and reconstituted with sterile water prior to use.

According to particular aspects, one or more of the above steps are optional.

EXAMPLE 4

Preparation of Thymus Extracts Thyex-4

Figure 4:
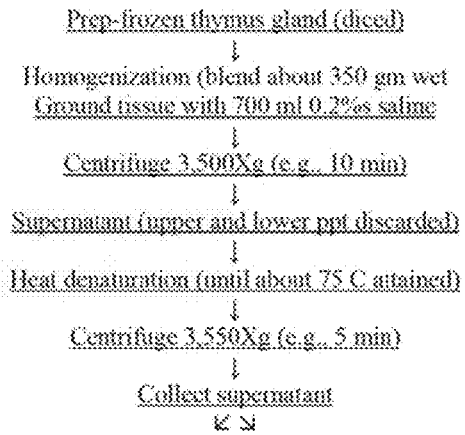
FIG. 4 is a flow diagrammatic representation comprising an inventive Thyex-4, -5, -6A, and -6B process embodiments for preparing a thymus extract composition.
Figure 4:
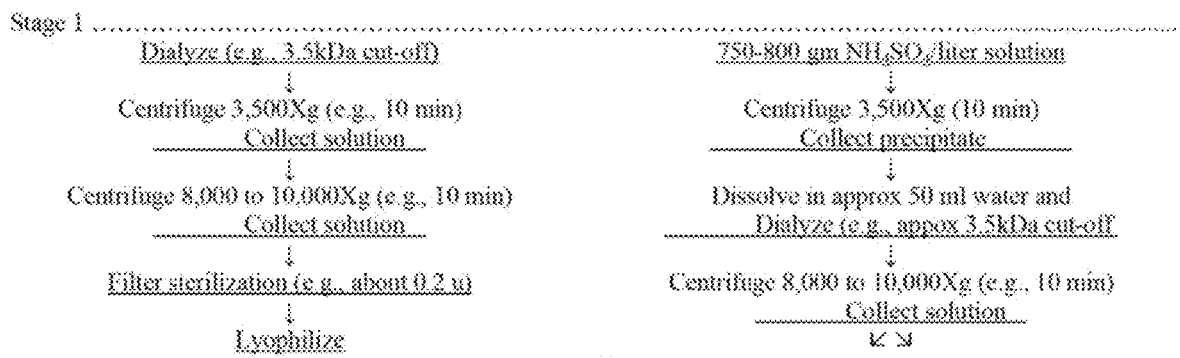
Figure 4:
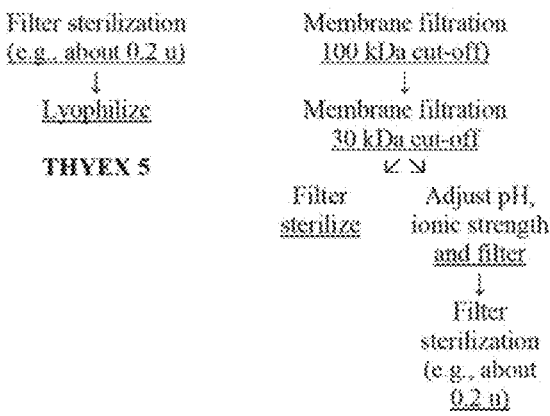

With reference to FIG. 4, this example provides an exemplary process embodiment used for preparing thymus extracts, and compositions ("Thyex-4") produced in accordance therewith suitable for oral delivery:

Thyex-4:

Thyex-4 process. The following steps (1)-(11) comprise a process embodiment for producing Thyex-4 (step (12) relates to storage), e.g., suitable for oral delivery (NOTE: the following steps (1)-(6) are referred to herein as "stage 1 steps (1)-(6)").

Stage 1 Steps (1)-(6):

(1) Homogenization of thymus tissue. Fresh "prime" (e.g., preferably not fibrous or whitish in appearance) porcine ovine or bovine thymus glands were frozen (e.g., overnight, or in some instances, preferably for at least 72 hours). The frozen glands were rinsed briefly in clean water and "dressed" by removal of any associated fibrous or connective tissue, fatty tissue, or lymph node tissue. The prime washed, dressed thymus glands were cut or minced into small pieces (e.g., about 1" to about 2" cubes using a sharp knife), and homogenized through the use of a food processor or other grinding apparatus (e.g., a meat grinder). For homogenization, a volume of approximately 700 ml of 0.2% NaCl solution (in distilled water) was blended for at least a minute with approximately 350 g wet weight of cut-up thymus tissue in a standard size blender to produce a thymus homogenate;

(2) Low-speed Centrifugation. The "thymus homogenate" of step (1) was centrifuged at about 3,500 rpm for 10 minutes at ambient temperature to produce a pellet and a supernatant fraction;

(3) Crude filtration. The resulting "supernatant fraction" of step (2) (after removal of any packed low density debris floating on its surface) was decanted from the centrifugation pellet and gravity filtered through one or more layers of standard cheese cloth to produce a primary filtered supernatant;

(4) Heat denaturation. The "primary filtered supernatant" of step (3) was heated to a temperature of about 75-80° C. by exposing the container thereof to a uniform heat source, such as a constant temperature water bath set at about 100° C., or a double boiler containing water at about 100° C. During said heating, the "primary filtered supernatant" was frequently agitated or stirred until it reached about 75-80° C. to produce a heat-denatured primary filtered supernatant;

(5) Low-speed Centrifugation. The "heat-denatured primary filtered supernatant" of step (4) was centrifuged at 3,500×g for 5 minutes at ambient temperature to produce a pellet and a heat-denatured supernatant fraction;

(6) Production of a "heat-denatured filtered supernatant." The "heat-denatured supernatant fraction" of step (5) was decanted from the centrifugation pellets and gravity filtered through one or more layers of standard cheese cloth to produce a filtered, heat-denatured supernatant fraction (hereinafter the "intermediate supernatant" fraction) that was still slightly warm from the heat denaturation of step (4);

Stage 2 Steps (7)-(6):

(7) Dialysis. The "intermediate supernatant" fraction of step (6) was dialyzed according to step (11) of the above-identified Thyex-1 process (e.g., using clean dialysis tubing (e.g., Spectrapor 3.5 kDa molecular weight cut-off size), and dialyzed with stirring (e.g., by means of a magnetically-driven stir bar in the dialysis chamber) for 3 days against an excess of distilled water at about 4° C.) to produce a dialyzed, intermediate supernatant fraction;

(8) Low-speed Centrifugation. The "dialyzed, intermediate supernatant fraction" of step (7) was centrifuged at 3,500 rpm for 5 minutes at ambient temperature to produce a pellet and a heat-denatured supernatant fraction;

(9) Production of a "heat-denatured filtered supernatant." The "heat-denatured supernatant fraction" of step (8) was decanted from the centrifugation pellets and gravity filtered through one or more layers of standard cheese cloth to produce a filtered, heat-denatured supernatant fraction;

(10) High-speed centrifugation. The "filtered, heat-denatured supernatant" fraction of step (9) was centrifuged at about 8,500×g for 5 minutes at ambient temperature to produce a pellet, and a high-speed supernatant fraction, Thyex-4;

(11) Filter sterilization. The "Thyex-4" fraction of step (10) was filter sterilized according to step (16) of the above-identified Thyex-1 process to produce sterile Thyex-4, suitable for oral delivery; and

(12) Storage. Thyex-4, produced in accordance with steps (1)-(11) of the Thyex-4 process was typically stored frozen (e.g., −5 to −20° C.) in sterilized containers, and thawed just prior to use. According to particular aspects, the therapeutic activity of Thyex-4 is stable to repeated freezing and thawing. Alternatively, Thyex-4 was lyophilized, stored at ambient temperature and reconstituted with sterile water prior to use.

According to particular aspects, one or more of the above steps are optional.

EXAMPLE 5

Preparation of Thymus Extracts Thyex-5

With reference to FIG. 4, this example provides an exemplary process embodiment used for preparing thymus extracts, and compositions ("Thyex-5") produced in accordance therewith suitable for oral delivery:
Thyex-5:

Thyex-5 process. The following steps (1)-(13) comprise a process embodiment for producing Thyex-5 (step (14) relates to storage), suitable for oral delivery:

(1)-(6) (See Stage 1 Steps (1)-(6) for Thyex-4 Above);

(7) Ammonium sulfate precipitation. About 750 to about 800 gm of ammonium sulfate was added to 1 L of the warm "intermediate supernatant" of step (6). The solution was stirred until all the ammonium sulfate was dissolved, and then allowed to stand for about 1 hour at ambient temperature to produce a salted intermediate supernatant fraction;

(8) Low-speed centrifugation. The "salted intermediate supernatant" of step (7) was divided between two, 1 L centrifuge bottles and centrifuged at 3,500×g for 10 minutes at ambient temperature to produce ammonium sulfate pellets, and supernatant fractions;

(9) Suspension of ammonium sulfate pellet fraction. The "ammonium sulfate supernatants" from step (8) were decanted from the centrifugation tubes and discarded, and excess salt solution was carefully wiped from the inside tube walls. The two ammonium sulfate pellets of step (8) (i.e., corresponding to each 1-L centrifuge bottle) were then suspended and dissolved by gentle mixing with about 50 ml of distilled water (or optionally with 0.01 to 0.05 M phosphate buffer (about pH 7)) for each pellet. The suspensions were allowed to stand for about 1 hour at ambient temperature with brief agitation about every 15 minutes (to facilitate complete dissolution of the pellets) to provide an ammonium sulfate fraction. Note that dissolution, if desired, of any remaining ammonium sulfate pellet can be affected by the step-wise addition of small amounts of distilled water (e.g., 5 ml aliquots), followed by agitation until the pellet is completely dissolved;

(10) Dialysis. The "ammonium sulfate" fraction of step (9) was transferred to clean dialysis tubing (e.g., Spectrapor 3.5 kDa molecular weight cut-off size), and dialyzed with stirring (e.g., by means of a magnetically-driven stir bar in the dialysis chamber) for 3 days against an excess of distilled water at about 4° C. to produce a dialyzed ammonium sulfate fraction. The distilled water was changed every 12 hours. Increasing hydrostatic pressure within the dialysis tubing was periodically relieved by removing some of the dialysate and transferring it to additional dialysis tubes;

(11) High-speed centrifugation. The "dialyzed ammonium sulfate fraction" of step (10) was centrifuged at 8,500×g for 10 minutes at ambient temperature to produce a pellet and dialyzed ammonium sulfate supernatant fraction (Thyex-5);

(12) Adjustment of pH and ionic strength. Optionally, about 5 ml of 1 M phosphate buffer (about pH 7) per liter is added to the "dialyzed ammonium sulfate supernatant fraction of step (11). Optionally, solid NaCl is then added to 0.85% (weight to volume) to produce a pH- and ionic strength-adjusted dialyzed ammonium sulfate supernatant fraction (Thyex-5);

(13) Filter sterilization. The "Thyex-5" of step (12) was filter sterilized by passage through a 0.2 micron membrane filter to produce sterile Thyex-5, suitable for oral delivery; and

(14) Storage. Thyex-5, produced in accordance with steps (1)-(13) of the Thyex-5 process, was typically stored frozen (e.g., −5° C. to −20° C.) in sterilized containers, and thawed just prior to use. According to particular aspects, the therapeutic activity of Thyex-5 was found to be stable to repeated freezing and thawing. Alternatively, Thyex-5 was lyophilized, stored at ambient temperature and reconstituted with sterile water prior to use.

According to particular aspects, one or more of the above steps are optional.

Above steps (7)-(11) are referred to herein as Stage 2 steps (7)-(11).

EXAMPLE 6

Preparation of Thymus Extracts Thyex-6A

Thyex-6A. With reference to FIG. 4, this example provides an exemplary process embodiment used for preparing thymus extracts, and compositions ("Thyex-6A") produced in accordance therewith suitable for oral delivery, or delivery as a topical ointment or by injection or inhalation:
Thyex-6A:

Thyex-6A process. The following steps (1)-(14) comprise a process embodiment for producing Thyex-6A (step (15) relates to storage), suitable for oral delivery:

(1)-(6) (see Stage 1 steps (1)-(6) for Thyex-4 and Thyex-5 above);

(7)-(11) (see Stage 2 steps (7)-(11) for Thyex-5 above);

(12) First exclusion-membrane filtration. The "dialyzed ammonium sulfate supernatant fraction" of step (11) was passed under nitrogen pressure at about 40-50 psi. (275.8 to 344.75 Kpa, in metric units) through a 100 kDa exclusion limit membrane filter (Amicon) at 4° C. (alternatively, ambient temperature will suffice) to produce a 3.5 kDa to 100 kDa filtrate;

(13) Second exclusion-membrane filtration. The "3.5 kDa to 100 kDa filtrate" of step (12) was passed under nitrogen pressure at 40 to 50 psi. (275.8 to 344.75 Kpa, in metric units) through a 30 kDa exclusion limit membrane filter (Amicon) to produce a 3.5 kDa to 30 kDa filtrate (Thyex-6A);

(14) Filter sterilization. The "Thyex-6A" of step (13) was filter sterilized by passage through a 0.2 micron membrane filter to produce sterile Thyex-6A, suitable for oral delivery, or delivery as a topical ointment or by injection or inhalation; and

(15) Storage. Thyex-6A, produced in accordance with steps (1)-(14) of the Thyex-6A process, was typically stored frozen (e.g., −5° C. to −20° C.) in sterilized containers, and thawed just prior to use. According to particular aspects, the therapeutic activity of Thyex-6A was found to be stable to repeated freezing and thawing. Alternatively, Thyex-6A was lyophilized, stored at ambient temperature and reconstituted with sterile water prior to use.

According to particular aspects, one or more of the above Steps are Optional.

EXAMPLE 7

Preparation of Thymus Extracts Thyex-6B

Thyex-6B process. With reference to FIG. 4, this example provides an exemplary process embodiment used for preparing thymus extracts, and compositions ("Thyex-6B") produced in accordance therewith suitable for oral delivery, or delivery as a topical ointment or by injection or inhalation:

Thyex-6B:

Thyex-6B process. The following steps (1)-(15) comprise a process embodiment for producing Thyex-6A (step (16) relates to storage), suitable for oral delivery, or delivery as a topical ointment or by injection or inhalation:

(1)-(6) (see Stage 1 steps (1)-(6) for Thyex-4, -5 and -6A above); (7)-(11) (see Stage 2 steps (7)-(11) for Thyex-5 and -6A above);

(12) First exclusion-membrane filtration. The "dialyzed ammonium sulfate supernatant fraction" of step (11) was passed under nitrogen pressure at about 40-50 psi. (275.8 to 344.75 Kpa, in metric units) through a 100 kDa exclusion limit membrane filter (Amicon) at 4° C. (alternatively, ambient temperature will suffice) to produce a 3.5 kDa to 100 kDa filtrate;

(13) Second exclusion-membrane filtration. The "3.5 kDa to 100 kDa filtrate" of step (12) was passed under nitrogen pressure at 40 to 50 psi. (275.8 to 344.75 Kpa, in metric units) through a 30 kDa exclusion limit membrane filter (Amicon) to produce a 3.5 kDa to 30 kDa filtrate (Thyex-6B);

(14) Adjustment of pH and ionic strength. Optionally, about 5 ml of 1 M phosphate buffer (about pH 7) per liter is added to the "dialyzed ammonium sulfate supernatant fraction of step (13). Optionally, solid NaCl is then added to 0.85% (weight to volume) to produce a pH- and ionic strength-adjusted dialyzed ammonium sulfate supernatant fraction (Thyex-6B);

(15) Filter sterilization. The "Thyex-6B" of step (14) was filter sterilized by passage through a 0.2 micron membrane filter to produce sterile Thyex-6B, suitable for oral delivery, or delivery as a topical ointment or by injection or inhalation; and

(16) Storage. Thyex-6B, produced in accordance with steps (1)-(15) of the Thyex-6B process, was typically stored frozen (e.g., −5° C. to −20° C.) in sterilized containers, and thawed just prior to use. According to particular aspects, the therapeutic activity of Thyex-6B was found to be stable to repeated freezing and thawing. Alternatively, Thyex-6B was lyophilized, stored at ambient temperature and reconstituted with sterile water prior to use.

According to particular aspects, one or more of the above steps are optional.

EXAMPLE 8

General Considerations for Practice of the Above-Identified Thyex 1-6A and -6B Process Embodiments This EXAMPLE 8 provides general considerations for practice of the above-identified Thyex 1-6A and -6B process embodiments.

The above-described embodiments (Thyex-1 (steps 1-16), Thyex-2 (steps 1-8), Thyex-3 (steps 1-10), Thyex-4 (steps 1-11), Thyex-5 (steps 1-13), Thyex-6A (steps 1-14), and Thyex 6B (steps 1-15)), and the storage (e.g., lyophilization) steps of the inventive processes may be practiced with various modifications (including but not limited to those outlined below) that are within the scope of the present invention, and with alternatives or substitutions that will be recognized by those of ordinary skill in the art as being equivalent to those used herein to produce Thyex 1-6A and -6B.

Thymus glands. In particular aspects, animals (e.g., steers) are taken to a packing house at about 12-14 months. The thymus gland at this age is grayish. As an animal ages, the gland begins to become fibrous and even whitish in color. The optimum yield of final product from one kilogram (about 4.5 lb) of prime gland is 1 gram of purified Thyex (e.g., Thyex 6A or 6B). Sheep glands are generally from 6 month-old animals.

Freshly harvested thymus glands from porcine, ovine, or bovine sources should optimally be frozen within 24 hours of harvest and stored frozen, preferably for at least 72 hours. Freezing of the thymus glands renders the cells more susceptible to disruption in isotonic or more preferably hypotonic (e.g., 0.2% to 0.3% salt, such as NaCl) salt solution during homogenization. Variations in the freezing temperature and duration are within the scope of the present invention. The thymus glands are preferably frozen at least once (e.g., −5 to −20° C.) for production of optimal extracts.

For example, to process, thawed glands are preferably first washed and extraneous materials, such as fatty tissues, lymph nodes, and connective tissues are preferably excised and discarded. The tissues are preferably minced into approximately 1" squares before subjected to grinding (e.g., in a food processor, meat grinder, blender, or equivalent or suitable device). Preferably, the ground glands are homogenized in a blender at a proportion of about 350 gm wet weight with 700 ml of 0.2% saline for at least a minute. Following centrifugation (e.g., about 3,500×g for 10 minutes), the supernatant solution (upper and lower ppt discarded) is heat denatured by raising the solution temperature in a double boiler with constant stirring to a temperature in the range of about 75° C. to 80° C. (preferably 75° C.). Following a second centrifugation at, e.g., the same speed but for 5 minutes, the supernatant solution is collected and precipitate (ppt) discarded. In particular embodiments, the glands for all Thyex processes 1, 2, 3, 4, 5, 6A, and 6B are processed through this phase in identical or very similar fashion.

Production of "secondary"- and "tertiary"-filtered supernatants, such as those described in step (4) of the Thyex-1 process embodiment, step (1) of the Thyex-2 process embodiment, or steps (4) and (5) of the Thyex-3 process embodiment, allows for more concentrated filtered supernatants (relative to the corresponding "primary"-filtered supernatants), thus reducing the amount of ammonium sulfate required (Thyex-1 process embodiment), or the lyophilization time required (Thyex-2 process embodiment) to process a given amount of thymus tissue. Generally, variations in the final protein concentrations (e.g., in the range of 1 to 7 mg/ml) of the various primary-, secondary- and tertiary-filtered supernatants reflect the average age of the animals from which thymus tissue is obtained. Preferably, the protein concentration of the tertiary-filtered supernatant is about 4 mg/ml.

A heat-denaturation step is integral to all of the above-described Thyex process embodiments, and facilitates precipitation and subsequent removal of relatively large, heat-labile proteins that have no utility in the claimed compositions or methods (see below). Variation in the volume of filtered supernatant fraction treated, in the final temperature of the heat-denaturation step (within the range of about 75° C. to about 80° C.), in the temperature of the uniform heat source (within the range of about 80° C. to about 100° C., preferably about 100° C.) and in the time period over which heating of the filtered supernatant fractions from initial to said final temperature takes place (generally within the range of about 5 to 20 minutes for a 1-liter volume of supernatant, but generally for lesser or greater periods of time when heating smaller or larger volumes, respectively) are within the scope of the present invention. Preferably, the supernatant is heated to the final temperature at a rate that is as rapid as possible whereby said rate, in combination with stirring, generally minimizes the occurrence of local supernatant temperatures (e.g., supernatant temperatures near the heat-transferring wall of the supernatant container) that exceed the desired final temperature.

Likewise, variations in the duration and frequency of stirring during said heating are within the scope of the present invention, and depend on the temperature of the constant-temperature heat source and the volume of supernatant being heated. Generally, both the duration and frequency of stirring increase with increasing supernatant volume or heat-source temperature. Constant stirring is also effective, and preferable when heating relatively large supernatant volumes.

Step (8) of the above-described Thyex-1 process embodiment, and step (7) of the above-described Thyex-5, -6A, and -6B process embodiments, involves protein concentration/fractionation by ammonium sulfate precipitation of the "intermediate supernatant" fraction. Most preferably, solid ammonium sulfate is added to attain high salt concentrations (e.g., in excess of about 0.7 gm/ml) with minimal dilution. Alternatively, this concentration/fractionation step is achieved by adding saturated ammonium sulfate solution. However, because dilution of the intermediate supernatant fraction is preferably minimized, this embodiment results in relatively lower final salt concentrations (e.g., of about 0.5 gm/ml or greater), and is thus less efficient in precipitating (and thereby recovering) desirable low molecular weight proteins. Nonetheless, according to particular aspects, the resulting Thyex compositions have activity in the claimed methods, albeit to a lesser degree. Moreover, the present invention also encompasses the use of combinations of saturated or sub-saturated ammonium sulfate solutions with solid ammonium sulfate.

A dialysis steps of the above-described Thyex process embodiments, allow any molecules of molecular weight less that about 3.5 kDa to pass through. Variation in the precise exclusion limit of the dialysis membrane is within the scope of the present invention. Generally, any dialysis membrane is acceptable provided that its exclusion limit (porosity) enables the retention of molecules having molecular weights of about 5 kDa or larger.

Additionally, variation in the precise exclusion limits of the filtration membranes used in membrane filtrations steps of the Thyex process embodiments are within the scope of the present invention. Generally, any such filtration membrane is acceptable provided that its exclusion limit (porosity) does not result in exclusion (i.e., removal from the final Thyex composition) of molecules having molecular weights equal to or smaller than about 15 kDa. For example, exclusion membranes that exclude molecules of about 20, 30 or 40 kDa or larger are useful in the practice of the present invention, but result in final Thyex compositions that are less active per mg of final protein, compared to those compositions prepared using an exclusion membrane the excludes proteins larger than about 15 kDa. Preferably, dialysis and filtration membranes are chosen such that the resulting Thyex compositions comprise proteins in the molecular weight range of about 5 to 14 kDa.

The process embodiments (e.g., Thyex-3) may further comprise fractionation, based on molecular weight, to obtain a final protein fraction having proteins of about 3.5 to about 30 kDa.

Many different types of membrane filters (e.g., cellulose acetate membranes; Millipore) are commercially available for use in filter sterilization procedures. Some commercially available membrane filters are self-contained and provided as pre-sterilized, disposable units. Other membranes are mounted in reusable membrane holders, and heat sterilized in an autoclave prior to use.

Preferably, the final Thyex 1-6A and -6B compositions are standardized at a protein concentration about 2 mg/ml, based on optical density at 260 and 280 nm. Preferred dosages are discussed herein above under "Dose Determinations."

The instant processes comprise steps to optimize protein compositions for therapeutic use. For example, the above-described Thyex 6A and Thyex 6B process embodiments are designed to provide therapeutic compositions suitable for delivery as a topical ointment or by injection or inhalation, and include ammonium sulfate precipitation/fractionation steps. Thyex-5 is prepared from a similar process but is somewhat less refined than Thyex-6A or Thyex-6B, and is designed to be preferably mixed in appropriate ratios with extracted lyophilized herbal sources and administered orally in, for example, filled gelatin capsules. The Thyex-4 process embodiment lacks ammonium sulfate precipitation step but provides for a sufficiently concentrated composition after lyophilization. The resulting Thyex-4 composition is less refined in relative to those of Thyex-5 (and Thyex-6A and -6B) but is nonetheless suitably concentrated and formulated for efficacious oral delivery in both animals and humans.

EXAMPLE 9

Treatment of Stomatitis (e.g., Gingivostomatitis) Using the Inventive Thyex Compositions and Combinations Thereof Overview. A thymic extract, Kyosenex® was used in management of a protracted case of feline gingivostomatitis. The patient responded dramatically, especially in the caudal portion of the oral cavity. The condition recurred upon stopping therapy and improved again on reinstituting the agent. Quality of life was greatly improved. Veterinarians are well acquainted with feline stomatitis, a syndrome of inflammation that can be frustrating to address (Healey, et al., 2007). The condition and its conventional diagnosis and management have been reviewed elsewhere (Lommer and Verstraete 2003; Belgard, et al., 2010; Dowers, et al., 2010; Lee, et al., 2010; Bhella, Corbee, 2011; Goodfellow, et al., 2011; Rennet, et al., 2011; Krishnan, et al., 2011). L-lysine may contribute to inflammation from viral issues in the caudal oral cavity. (Drazenovich, et al., 2009). This EXAMPLE 9 demonstrates utility of administration of Applicant's thymus extract composition in the treatment of stomatitis (e.g., gingivostomatitis).

Subject. A thirteen-year-old, spayed female, domestic short haired cat presented for a chronic history of hyperthyroidism managed with methimazole. A complete blood count, urinalysis, FeLV, Fiv, and T-4 were normal. The cat's chronically recurring rhinitis and sinusitis had been medically managed using a wide variety of medical therapies including antibiotics (selected empirically and via culture and sensitivity and used for extensive periods of time), antihomotoxic and homeopathic agents, nutritional therapies including L-lysine and medical mushrooms, novel antigen diets, herbal agents, acupuncture, and essential oils.

A few months before, the cat presented with difficulty eating and was diagnosed with chronic stomatitis. At the recommendation of the general practice veterinarian the cat was seen and treated by a boarded veterinary dentist with dental radiographs, dental prophylaxis, multiple extractions, and antibiotics. The cat did improve for a short period of time following therapy, but oral cavity pain and inflammation returned shortly after its therapy. The owners declined immunosuppressive therapies as their prior cat had died of cancer and they wished to preserve the cat's immune integrity.

A discussion of the condition, its recurring nature and frustrating recurrence rates ensued. Herpes or other viral infections were strongly suspected as inciting cause in this cat and the owners understood that cure was unlikely. It was agreed to initiate treatment.

Dose. The thymus extract employed (Kyosenex®) was available in oral use form and injectable form. Since the cat was hard to medicate, we opted for ubcutaneous injection. One vial of lyophylized thymic extract was hydrated with 2.0 cc of diluent (standard saline; final protein concentration about 2 mg/ml). The cat was given a five day cycling dosing pattern that consisted of giving 0.2 cc of this mixture by subcutaneous injection daily for three days and skipping two days before repeating the cycle again. During this time the cat also received acupuncture weekly for three total treatments. After a month, the dose was reduced to 0.1 cc daily for three days, off for two days and repeated in five day cycles.

Results. Patient comfort improved rapidly. Nine days after beginning injections the cat was able to open her mouth arid began eating. Her owners reported she began playing and purring again. Erythema and pain were both reduced and continued to improve for two months. Her sinusitis would flare but her oral cavity did well until she developed an invasive nasal mass. The owners declined biopsy but CT revealed a mass eroding into the skull from the nasal passage. Carcinoma was suspected by the internist. The owners continued to manage her condition with multi-modal CAVM therapies and the cat did well until her euthanasia eight months later. Her owners were very happy with her therapy. The following figures illustrate the cat's condition and progress.

Figure 5:
FIG. 5 shows day one of therapy for gingivostomatitis using Applicant's thymus extract composition.

FIG. 5 shows day one of therapy. Note multiple extractions and excellent healing from prior dental care. At this time gingivostomatitis-related inflammation is very visible, and the patient objected strongly to opening her mouth.

Figure 6:
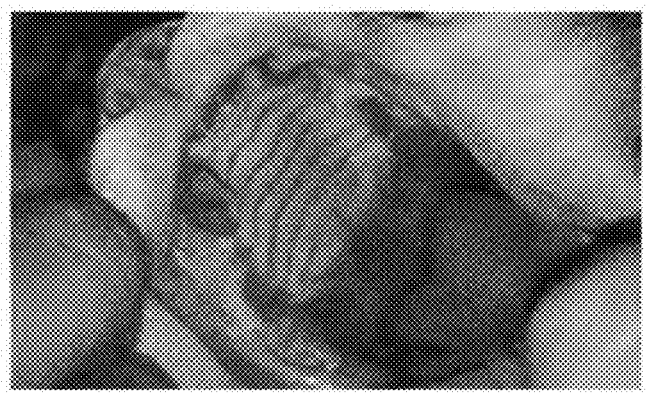
FIG. 6 shows thirty days of therapy for gingivostomatitis using Applicant's thymus extract composition (6×5 day cycles).

FIG. 6 shows thirty days of therapy (6×5 day cycles). Only some residual inflammation is still present, and the mouth is far less red and far more comfortable. Cat was eating well and playing at this exam. She did not object to opening her mouth.

Figure 7:
FIG. 7 shows sixty days of therapy for gingivostomatitis using Applicant's thymus extract composition (12×5 day cycles).

FIG. 7 shows sixty days of therapy (12×5 day cycles). Some residual inflammation is still present, particularly in the incisor and canine tooth regions, but the pharyngeal area is nearly normal.

Discussion. This case demonstrates a striking response to a novel thymic extract. The treatment is not curative but greatly reduced gingivostomatitis-related inflammation and patient discomfort as evidenced by the cat's behavior, appetite and activity levels. The owners reported that the cat behaved as if she were five years younger while on this treatment. She received the injections off and on for a year with no sign of adverse effects. The veterinarian has subsequently treated several more cases of chronic gingivostomatitis in cats using this agent with similar good results. In the veterinarian's experience, this condition should be addressed in a systematic and thorough manner with the aid of a qualified, preferably board-certified veterinary dentist.

While the animal had also received various homeotpathic treatments, the gingivostomatitis condition was never reversed until Kyosenex® treatment was initiated.

According to additional aspects, treatment of stomatitis (e.g., gingivostomatitis) with thymus extracts (e.g., Thyex-1-Thyex 6A and Thyex-6B, Kyosenex®) in combination with at least one additional agent is provided. For example treatment using thymus extract in combination with at least one of antibiotics, medicated mouth rinses, salt water, hydrogen peroxide, xylocaine, antiviral agents, aciclovir, fluid intake, good oral hygiene, gentle debridement of the mouth, etc., is provided.

In this example, since the cat was somewhat difficult to handle and thus hard to medicate, the thymus extract was used in an injectable form. Likewise, similar therapeutic efficacy was achieved in multiple additional animal subjects using oral administration of the thymus extract (in an orally deliverable form as described herein). According to further aspects, administration by injection, oral administration, inhalation, topically, or rectal administration is efficacious in treating stomatitis (e.g., gingivostomatitis) with thymus extracts (e.g., Thyex-1-Thyex 6A and Thyex-6B, Kyosenex®), including in combination with at least one additional agent.

References Cited in EXAMPLE 9

Belgard, et al., *Berl Munch Tierarztl Wochenschr*, Sepember-October 2010, 123(9-10):369-76.

Bhella, et al., *J Anim Physiol Anim Nutr* (Berl), Jul. 18, 2011, doi:10.1111/j 0.1439-0396.2011.01195.x.

Dolieslager, et al., *Vet Microbiol.*, Feb. 24, 2011, 148(1):93-8.

Dowers, et al., *J. Feline Med Surg.*, April 2010, 12(4):314-21.

Drazenovich, et al., *Am J Vet Res.*, November 2009, 70(11): 1391-400.

Goldstein, R., Wiley-Blackwell Publishing, pp. 277-291 and 669.

Hargis & Ginn., *Vet Clin North Am Small Anim Pract.*, November 1999, 29(6):1281-90.

Healy, et al., *J Feline Med Surg.*, October 2007, 9(5):373-81.

Hennet, et al., *J Feline Med Surg.*, August 2011, 13(8):577-87.

Ioannou, et al., *Cancer Immunol Immunother.*, May 2012, 61(5):599-614.

Krishnan, et al., *Eur Rev Med Pharmacal Sci.*, June 2011, 15(6):673-81.

Lee, et al., *Feline Med Surg.*, February 2010, 12(2):72-9.

Lommer and Verstraete., Oral Microbial Immunol., April 2003, 1(2):131-4.

EXAMPLE 10

Treatment of Demodectic Mange Using the Inventive Thyex Compositions and Combinations Thereof Overview. A thymic extract, Kyosenex® was used in management of a protracted case of canine demodectic mange. The patient responded dramatically. At one-year post treatment, there has been no recurrence of the condition.

Subject. A 1.5-year-old 65 lb. intact female pit bull was relinquished to the animal control unit due to severe skin problems. She had whelped 4 weeks earlier, and her puppies were similarly affected. She was examined and diagnosed with severe generalized demodectic mange, bacterial pruritus and dermatophytosis.

Figure 8:
FIG. 8 shows arrival of demodectic mange patient at the animal control unit prior to Kyosenex® treatment.

FIG. 8 shows arrival of demodectic mange patient at the animal control unit prior to Kyosenex® treatment. Treatment had been initiated a week earlier with oral ivermectin (0.5 cc PO SID). However, ivermectin is a broad-spectrum antiparasitic agent, traditionally against worms. More recent evidence supports its off-label use against arthropods. The main concern is neurotoxicity, which in most mammalian species may manifest as central nervous system depression, and consequent ataxia, as might be expected from potentiation of inhibitory GABA-ergic synapses. Dogs with defects in the P-glycoprotein gene can be severely poisoned by ivermectin. Moreover, this patient was not responding to ivermectin, and her condition was worsening.

Figure 9:
FIG. 9 shows initiation of Kyosenex® treatment; Day 1 (day 7 of ivermectin treatment).

Therefore, a holistic veterinary consult was requested by animal control. The veterinarian accepted the dog for the Thymus extract (Kyosenex®) treatment protocol. Upon initial exam, the patient appeared edgy, anxious and exhibited a short episode of aggressive loud barking and behavior toward the examining doctor. The skin was moist, thickened, hyperemic and erythemic, and exhibited nearly total alopecia (FIG. 9). Facial and truncal skin exhibited excessive skin folds and hyperemic and erythemic pustules. The periorbital and pinnal tissue was similarly affected with edema and erythema.

Dose. Kyosenex® was initiated at 0.5 cc subcutaneous injections three times a week. One vial of lyophylized thymic extract was hydrated with 2.0 cc of diluent (standard saline; final protein concentration about 2 mg/ml).

Figure 10:
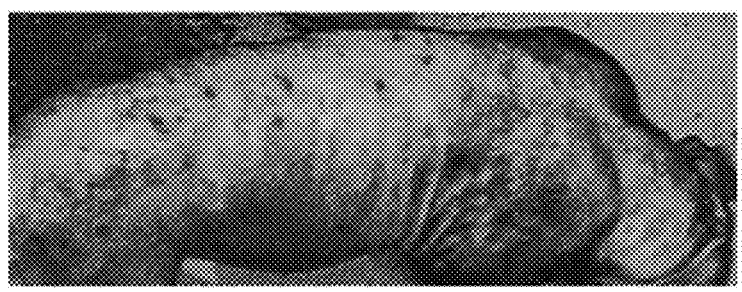
FIG. 10 shows day 8, beginning of second week of Kyosenex® treatment (3 injections total).

Results. FIG. 8 shows arrival of demodectic mange patient at the animal control unit prior to Kyosenex® treatment. FIG. 9 shows initiation of Kyosenex® treatment; Day 1 (day 7 of ivermectin treatment). Facial and truncal skin exhibited excessive skin folds and hyperemic and erythemic pustules. Examination after one week of treatment revealed a dramatic improvement, with beginning regrowth of the hair coat and significant decrease in skin pustules, erythema and edema (FIG. 10). FIG. 10 shows day 8, beginning of second week of Kyosenex® treatment (3 injections total).

Patient attitude was improving as well. There was no evidence of any irritability or aggression. She was friendly and compliant with treatment.

Figure 11:
FIG. 11 shows day 15, beginning of third week of Kyosenex® treatment (6 injections total).
Figure 12:
FIG. 12 shows day 22, beginning of fourth week of Kyosenex® treatment (9 injections total).

The treatment protocol continued for a total of 28 days. The response to therapy was striking in both the improvement and rapidity of symptom resolution (FIGS. 11 and 12). FIG. 11 shows day 15, beginning of third week of Kyosenex® treatment (6 injections total). FIG. 12 shows day 22, beginning of fourth week of Kyosenex® treatment (9 injections total). Haircoat regrowth progressed quickly with rapid response of alopecia and secondary dermatitis. Excessive facial skin folds and pronounced periocular and pinnal alopecia and erythema also resolved.

Figure 13:
FIG. 13 shows day 28, after discontinuation of Kyosenex® treatment (12 injections total). Note, in comparison with FIGS. 10 and 11, the regrowth of haircoat along the trunk.
Figure 14:
FIG. 14 shows patient in her permanent home, 2-months post-treatment with Kyosenex®.

She was examined again after discontinuation of therapy (FIG. 13). FIG. 13 shows day 28, after discontinuation of Kyosenex® treatment (12 injections total). Note, in comparison with FIGS. 10 and 11, the regrowth of haircoat along the trunk. At that time (day 28), the hair coat looked normal. The patient appeared happy, friendly, exuberant, and interacted well with other dogs and people. The rapidity and extent of response when Kyosenex® was added to her initial treatment protocol was much more significant than expected based on experience with the use of ivermectin only. Shortly after her treatment protocol was completed, the patient was adopted to a permanent home (FIG. 14). At one-year post treatment, there has been no recurrence of the condition. FIG. 14 shows patient in her permanent home, 2-months post-treatment with Kyosenex®.

According to additional aspects, treatment of demodectic mange with thymus extracts (e.g., Thyex-1-Thyex 6A and Thyex-6B, Kyosenex®) in combination with at least one additional agent is provided. For example treatment using thymus extract in combination with at least one of rotenone, Goodwinol (a rotenone-based insecticide ointment), antibiotics, medicated shampoos, Amitraz (a parasiticidal dip), avermectins, ivermectin, doramectin, milbemycin, and sulfurated lime, etc., is provided.

In this example, the thymus extract was used in an injectable form (subcutaneous injection). According to additional aspects, similar therapeutic efficacy is achieved using other administration routes, including oral administration of the thymus extract (in an orally deliverable form as described herein). According to further aspects, administration by injection, oral administration, inhalation, topically, or rectal administration is efficacious in treating demodectic mange with thymus extracts (e.g., Thyex-1-Thyex 6A and Thyex-6B, Kyosenex®), including in combination with at least one additional agent.

EXAMPLE 11

Treatment of Additional Cases of Demodectic Manage with Kyosenex®

An additional five dogs having previously untreatable demodectic mange were treated as described in EXAMPLE 10, using daily doses of between 1.0 and 3.0 ml of Kyosenex® (each vial of lyophylized thymic extract was hydrated with 2.0 cc of diluent prior to injection).

A favorable response was seen in 3/5 animals treated (60%). While all of the animals had also been receiving various homeotpathic treatments (e.g., Traumeel, Homotox, SBGA), the chronicity of the condition was never reversed until Kyosenex treatment was initiated.

| Patient | Dose Kyosenex ® | Administration Frequency and duration | Outcome |
| --- | --- | --- | --- |
| Australian Shepard mix (21 months; 40 lbs.) | 1.0 ml | (twice/week) for 7 months | Excellent |
| Pit bull mix (9 months; 24 lbs.) | 1.0 | (twice/week) for 1 months | Good |
| Boxer mix 5 year; 71 lbs.) | 1.0 | (twice/week) for 1 months | Inconclusive |

-continued

| Patient | Dose Kyosenex ® | Administration Frequency and duration | Outcome |
|---|---|---|---|
| Labrador (5 year; 83 lbs.) | 3.0 | (once/week) for 2 months | Excellent |
| German Shepard (10 year; 65 lbs.) | 1.5 | (twice/week) for 2 months | Treatment ongoing |

EXAMPLE 12

Treatment Synergies with the Inventive Thyex Compositions and Combinations Thereof According to particular aspects of the present invention, administering the inventive Thyex compositions along with at least one other antibacterial, antifungal, antiviral agent and/or along with a polysaccharide extract to stimulate macrophage achieves a most treatment response. In certain aspects, administration of Thyex extract alone is sufficient.

According to particular aspects, treatment of stomatitis (e.g., gingivostomatitis) with thymus extracts (e.g., Thyex-1-Thyex 6A and Thyex-6B, Kyosenex®) in combination with at least one additional agent is provided. For example treatment using thymus extract in combination with at least one of antibiotics, medicated mouth rinses, salt water, hydrogen peroxide, xylocaine, antiviral agents, aciclovir, fluid intake, good oral hygiene, gentle debridement of the mouth, colostrum, etc., is provided.

According to particular aspects, treatment of demodectic mange with thymus extracts (e.g., Thyex-1-Thyex 6A and Thyex-6B, Kyosenex®) in combination with at least one additional agent is provided. For example treatment using thymus extract in combination with at least one of rotenone, Goodwinol (a rotenone-based insecticide ointment), antibiotics, medicated shampoos, Amitraz (a parasiticidal dip), avermectins, ivermectin, doramectin, milbemycin, and sulfurated lime, colostrum, etc., is provided.

Beta glucans. According to particular aspects, polysaccharides, such as beta glucan consisting of complex sugars found in cell walls of yeasts and mushrooms, are a preferred agent in combination with the inventive Thyex compositions, and act synergistically in combating demodectic mange and stomatitis (e.g., gingivostomatitis) and other related conditions.

There are three forms of beta glucan based on the linkages of the complex sugars, and these are recognized as beta-1,3 or 1,4, and 1,6 glucan. Most are in the form of 1,3 and 1,4, or 1,3 and 1,6, but the 1,3 form, which is most abundant in the fruiting bodies of certain mushrooms (e.g., *Sparassis crupa* or Cauliflower mushroom; or *Lentinula edodes* or shitake, etc.). Typically, marketing strategies relating to marketing glucan (typically from the cell wall of the common yeast) emphasize "enhanced the immune system," "increases antibody production," and "fight cancer."

A reference by Ohno, Miura, Nakajima, and Yadomae (2000, Biol. Phar. Bull. 23:866-872) describes a procedure for extracting beta glucan from shitake mushroom. Recently, two firms in Japan have successfully cultured the cauliflower mushroom (aka Hanabaritake), and the Applicant has obtained cauliflower mushroom powder form from these firms.

According to particular aspects, a preferred polysaccharide comprises one or more of the beta glucans, including three types based on the linkages: 1-3, 1-4, and 1-6). A number of commercial beta glucan products are available with most being derived from the common yeast. According to particular aspects, however, the preferred sources are mushrooms; with shitake being most common because of its ready availability/source, and cauliflower mushroom (*Sparassis crupa*), which is preferred as it contains beta 1-3 glucans, but unfortunately has limited availability. Additionally, the shitake mushroom, which is most widely available, is reported to contain the 1-3 glucan and chitin.

According to particular aspects, an oral route of administration is favorable, possibly because the intestinal walls are sites containing large amounts of lymph nodes and thus T cells.

Additional Combination Agents and/or Therapies:

Colostrum formulations. Additional combinations of the thymus extracts with colostrum (e.g., bovine colostrum) are disclosed herein (see working EXAMPLE 13), and provide for reducing itching as described herein.

In particular aspects, bovine colostrum is used to formulate the thymus extract for administration, and in certain embodiments, first milking bovine colostrum is used (e.g., "First Milking Bovine Colostrum" from Immuno-Dynamics, Fennimore, Wis.; sold as "ID-1" optionally with methyl paraben and/or propyl paraben as preservative).

According to particular aspects Kyosenex® PRIME Canine is formulated (formulated for Applicant by Immuno-Dynamic & URL Laboratories, Fennimore, Wis. USA, using ID-1 serum ("Bovine IgG Colostrum Serum")) using 66.6 ug of Kyosenex/ml colostrum and administered in 7/10 ml (0.7 ml) per spray or dropwise, twice daily, 1 spray for each 15 lbs until resolution of condition, and then twice a week thereafter for maintenance.

According to particular aspects Kyosenex® PRIME Feline is formulated (formulated for Applicant by Immuno-Dynamic & URL Laboratories, Fennimore, Wis. USA, using ID-1 serum ("Bovine IgG Colostrum Serum")) using 66.6 ug of Kyosenex/ml colostrum and administered in 7/10 ml (0.7 ml) per spray or dropwise, twice daily, 1 spray for each 15 lbs until resolution of condition, and then twice a week thereafter for maintenance.

According to particular aspects Kyosenex® PRIME Avian is formulated (formulated for Applicant by Immuno-Dynamic & URL Laboratories, Fennimore, Wis. USA, using ID-1 serum ("Bovine IgG Colostrum Serum")) using 66.6 ug of Kyosenex®/ml colostrum and administered in 7/10 ml (0.7 ml) per spray or dropwise, twice daily, 1 spray for each 15 lbs until resolution of condition, and then twice a week thereafter for maintenance.

As indicated above, preferred aspects comprise treatment of demodectic mange and stomatitis (e.g., gingivostomatitis), or treatment of itching using Thyex compositions in optional combination with colostrum and/or other fungal and/or herbal preparations, etc., including the following:

*Paresis crepe* (aka cauliflower mushroom or hanabaritake) preparations, comprising beta 1-3 glucan, can be used to stimulate macrophage in combination with the inventive Thyex compositions.

*Lentinula edodes* (shitake; e.g., alkaline digest according to the procedure reported by Ohno, et al. (Biol. Phar. Bull. 23:866-872, 2000), comprises beta 1-3 glucan and chitin, and can be used for treating age-related illness in combination with the inventive Thyex compositions.

*Astralagas membranaceus* (*Scutellaria baicalensis, Houttuynia cordata*; hot water extract of ground herbs and secondary extraction by alkaline digest as above), stimulate macrophages, and can be used for treating age-related illness in combination with the inventive Thyex compositions.

*Liilium longiforum* (aka Easter lily; to prepare extract, leaves are pre-frozen, blended (homogenized) in water, and boiled. The liquid extract centrifuged and the supernatant solution distilled (approximately one-half volume is collected)), can be used for treating age-related illness in combination with the inventive Thyex compositions.

*Houttuynia cordata* (as mentioned above) extracts from leaves (see Applicant's U.S. Pat. No. 8,609,824), incorporated by reference herein in its entirety for teaching on *Houttuynia cordata* extracts) can be used for treating age-related illness in combination with the inventive Thyex compositions. According to particular aspects, *Houttuynia cordata* has substantial utility to treat nausea in both humans and animals caused by illnesses, infections, or other treatments, and in particular embodiments is used in combination with one or more of the inventive Thyex compositions, plus or minus standard additional drugs.

Treatment in combination with at least one of traumeel, homotox, SBGA (blue green algae), placenta, wobenzyme, spascupreel, IMM formula, yunnan paiyo, vitamin E, omega-3 fatty acids, semongrass oil, and cedar oil is also provided.

EXAMPLE 13

Treatment Using Thyex Compositions in Combination with Colostrum was Effective in Reducing Allergic Itching Overview. A thymic extract (Kyosenex®) was formulated with colostrum and used in management of a severe case of canine itching relating to allergy. The patient responded dramatically and favorably.

Subject. A male dog showing allergic symptoms, presented with pruritic, red skin accompanied by sever itching and inflammation.

The veterinarian accepted the dog for a Thymus extract (Kyosenex®)/colostrum formulation treatment protocol.

Formulation and Dose. Kyosenex® was formulated with colostrum. Specifically, for this example, Kyosenex® PRIME Canine was formulated (formulated for Applicant by Immuno-Dynamic & URL Laboratories, Fennimore, Wis. USA, using ID-1 serum ("Bovine IgG Colostrum Serum")) using 66.6 ug of Kyosenex®/ml colostrum and administered in 7/10 ml (0.7 ml) per spray or dropwise, twice daily, 1 spray for each 15 lbs subject weight until resolution of condition, and then twice a week thereafter for maintenance.

Results. After only two treatments, the itch level and degree of inflammation markedly improved. The patient was friendly and compliant with treatment.

The treatment protocol continued for a total of 5 days, with improvement each day. The rapidity and extent of response when the Kyosenex®/colostrum formulations was administered was dramatic, and much more significant than expected based on experience with the use of other agents, including compared with experience based on use of homeopathic remedies and/or Kyosenex® alone.

According to additional aspects, treatment of itching with thymus extracts (e.g., Thyex-1-Thyex 6A and Thyex-6B, Kyosenex®) in combination with colostrum is provided. The two can be administered as separate agents, and can be formulated together as in this example.

In this example, the thymus extract colostrum formulation was administered in an aerosol (oral spray) form. According to additional aspects, similar therapeutic efficacy is achieved using various administration routes, including administration orally, injection, inhalation, topically, or rectal administration is efficacious in treating itching with thymus extracts (e.g., Thyex-1-Thyex 6A and Thyex-6B, Kyosenex®) formulated with colostrum, including in combination with at least one additional agent (e.g., herbs or homeopathics).

As will be appreciated by one of ordinary skill in the art, the dosage administered will vary, depending upon the size, needs and responsiveness of the subject. For example, while 66.6 ug of Kyosenex®/ml colostrum is typical, less Kyosenex®/ml colostrum can be used. For example, 33.3 ug Kyosenex®/ml colostrum can be used, or 15 ug Kyosenex®/ml colostrum can be used. Generally, the amount of Kyosenex®/ml colostrum can vary between 5 to 100 ug of Kyosenex®/ml colostrum, more preferably between 10 to 80 ug of Kyosenex®/ml colostrum, even more preferably between 20 to 80 ug of Kyosenex®/ml colostrum, and most preferably between 30 to 70 ug of Kyosenex®/ml colostrum is used. Optionally, preservatives (e.g., methyl paraben and/or propyl paraben) can be included.

According to particular aspects of the present invention, the dramatic efficacy of the thymic extract/colostrum formulations were surprising, and while not being bound by mechanism, colostrum may serve, inter alia, as a mucosal coating that increases the tissue exposure of the Kyosenex® polypeptides, and thereby increasing absorption.

The various methods and techniques described above provide a number of ways to carry out the application. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some preferred embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

In some embodiments, the numbers expressing quantities of ingredients, properties such as molecular weight, reaction conditions, and so forth, used to describe and claim certain embodiments of the application are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

In some embodiments, the terms "a" and "an" and "the" and similar references used in the context of describing a particular embodiment of the application (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. No language in the specification should be construed as indicating any non-claimed element essential to the practice of the application.

Preferred embodiments of this application are described herein. Variations on those preferred embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

The invention claimed is:

1. A composition, comprising an effective amount of thymus gland extract fractionated to remove proteins greater than 30 kDa and less than 3.5 kDa, in combination with bovine colostrum.

2. The composition of claim 1, wherein the thymus gland extract and the colostrum are bovine.

3. The composition of claim 2, wherein the bovine colostrum comprises first milking colostrum.

4. The composition of claim 1, wherein the composition is a therapeutic composition.

5. The composition of claim 1, wherein the thymus gland extract comprises a heat-treated, fractionated thymus gland extract.

6. The composition of claim 1, wherein the bovine colostrum comprises first milking colostrum, second milking colostrum or third milking colostrum.

7. The composition of claim 1 as part of a pharmaceutical composition, or a pharmaceutically acceptable salt thereof, and optionally a pharmaceutically acceptable carrier or diluent.

8. The pharmaceutical composition of claim 7, wherein the thymus gland extract comprises a heat-treated, fractionated thymus gland extract.

9. The pharmaceutical composition of claim 7, wherein the thymus gland extract and the colostrum are bovine.

10. The pharmaceutical composition of claim 7, wherein the bovine colostrum comprises first milking colostrum, second milking colostrum, or third milking colostrum.

11. The composition of claim 9, wherein the bovine colostrum comprises first milking colostrum.

12. The pharmaceutical composition of claim 7 formulated as a liquid, gel, syrup, or a slurry.

13. A method of treating itching, comprising administering to a subject in need thereof a therapeutically effective amount of a fractionated thymus gland extract composition in combination with or formulated with bovine colostrum, for reducing itching in the subject, wherein the thymus gland extract has been fractionated to remove proteins greater than 30 kDa and less than 3.5 kDa.

14. The method of claim 13, wherein the itching is caused by allergy.

15. The method of claim 13, wherein the itching is caused by parasites.

16. The method of claim 15, wherein the itching comprises itching in demodicosis.

17. The method of claim 16, wherein the demodicosis is that of canine demodicosis.

18. The method of claim 17, wherein the canine demodicosis comprises that caused by *Sarcoptes scabiei*.

19. The method of claim 16, wherein the demodicosis is that of feline demodicosis.

20. The method of claim 19, wherein the feline demodicosis comprises that caused by *Demodex cati*.

21. The method of claim 19, wherein the feline demodicosis comprises that caused by *Demodex gatoi*.

22. The method of claim 15, wherein the itching comprises itching in stomatitis.

23. The method of claim 22, wherein the stomatitis is gingivostomatitis.

24. The method of claim 15, wherein the itching is dermatophytosis.

25. The method of claim 1, wherein the thymus gland extract/colostrum combination or formulation is administered at least twice per day for at least two days.

26. The method of claim 25, wherein the thymus thymus gland extract/colostrum composition or formulation is administered twice per day for at least two days, and then at least twice per week for at least one month.

27. The method of claim 25, wherein the thymus gland extract/colostrum composition or formulation is administered at least twice per day for at least a week.

28. The method of claim 1, wherein the thymus gland extract/colostrum composition comprises proteins or polypeptides having molecular weights within 5 to 14 kDa.

29. The method of claim 1, wherein the bovine colostrum comprises first milking colostrum, second milking colostrum, or third milking colostrum.

30. The method of claim 1, further comprising treating with at least one additional anti-parasitic, anti-bacterial, anti-fungal, anti-viral agent, or homeopathic agent.

31. The method of claim 30, wherein the at least one anti-parasitic agent comprises an avermectin.

32. The method of claim 31, wherein the avermectin comprises at least one of ivermectin, doramectin, and/or milbemycin.

33. The method of claim 32, wherein the avermectin comprises ivermectin.

34. The method of claim 30, wherein, the at least one anti-bacterial agent comprises an antibiotic, metronidazole, tinidazole, co-trimoxazole, cephamandole, ketoconazole, latamoxef, cefoperazone, amoxicillin, cefmenoxime, furazolidone, doxycycline, and erythromycin.

35. The method of claim 30, wherein the at least one anti-fungal agent comprises one or more of itraconazole, Terbinafine, clotrimazole, fluconazole, ketoconazole, griseofulvin, econazole, miconazole, miconazole nitrate, tolnaftate, thiabendazole, lime-sulfur treatments, imidazoles, (eg., triazoles, isavuconazole, ravuconazole, posaconazole, voriconazole, terconazole, thiazoles, abafungin , allylamines, amorolfine, naftifine, butenafine, echinocandins, anidulafungin, caspofungin, and/or micafungin.

36. The method of claim 30, wherein the at least one anti-viral agent comprises at least one of combivir, boceprevir, abacavir, docosanol, aciclovir, didanosine, cidofovir, acyclovir, delavirdine, adefovir, amantadine, amprenavir, arbidol, darunavir atazanavir, atripla, zanamivir, or oseltamivir.

37. The method of claim 30, wherein the at least one homeopathic agent comprises at least one of traumeel, blue green algae, placenta, vitamin E, omega-3 fatty acids, lemongrass oil, and/or cedar oil.

38. The method of claim 1, wherein administration is by at least one route selected from the group consisting of oral administration, injection, inhalation, topical application, and rectal administration.

39. The method of claim 38, wherein administration is by at least one route selected from the group consisting of oral administration and injection.

40. A method for treating parasite-mediated inflammation, comprising administering to a mammalian subject in need thereof a therapeutically effective amount of a fractionated thymus gland extract composition, in combination with or formulated with bovine colostrum, for reducing parasite-mediated inflammation in the subject, wherein the thymus gland extract has been fractionated to remove proteins greater than 30 kDa and less than 3.5 kDa.

41. The method of claim 40, wherein the parasite-mediated inflammation comprises inflammation in demodicosis.

42. The method of claim 41, wherein the demodicosis is that of canine demodicosis.

43. The method of claim 42, wherein the canine demodicsis comprises that caused by *Sarcoptes scabiei*.

44. The method of claim 41, wherein the demodicosis is that of feline demodicosis.

45. The method of claim 44, wherein the feline demodicosis comprises that caused by *Demodex cati*.

46. The method of claim 44, wherein the feline demodicosis comprises that caused by *Demodex gatoi*.

47. The method of claim 40, wherein the parasite-mediated inflammation comprises inflammation in stomatitis.

48. The method of claim 47, wherein the stomatitis is gingivostomatitis.

49. The method of claim 40, wherein the parasite-mediated inflammation comprises inflammation in dermatophytosis.

50. The method of claim 40, wherein the composition is administered at least once per month for at least one month.

51. The method of claim 50, wherein the composition is administered at least once per week for at least one month.

52. The method of claim 50, wherein the composition is administered at least twice per week for at least one month.

53. The method of claim 40, wherein the thymus gland extract/colostrum composition comprises proteins or polypeptides having molecular weights within 5 to 14 kDa.

54. The method of claim 40, further comprising treating with at least one additional anti-parasitic, anti-bacterial, anti-fungal, anti-viral agent, or homeopathic agent.

55. The method of claim 54, wherein, the at least one anti-parasitic agent comprises an avermectin.

56. The method of claim 55, wherein the avermectin comprises at least one of ivermectin, doramectin, and/or milbemycin.

57. The method of claim 56, wherein the avermectin comprises ivermectin.

58. The method of claim 54, wherein, the at least one anti-bacterial agent comprises an antibiotic, metronidazole, tinidazole, co-trimoxazole, cephamandole, ketoconazole, latamoxef, cefoperazone, amoxicillin, cefmenoxime, furazolidone, doxycycline, and erythromycin.

59. The method of claim 54, wherein the at least one anti-fungal agent comprises one or more of itraconazole, Terbinafine, clotrimazole, fluconazole, ketoconazole, griseofulvin, econazole, miconazole, miconazole nitrate, tolnaftate, thiabendazole, lime-sulfur treatments, imidazoles, (eg., triazoles, isavuconazole, ravuconazole, posaconazole, voriconazole, terconazole, thiazoles, abafungin , allylamines, amorolfine, naftifine, butenafine, echinocandins, anidulafungin, caspofungin, and/or micafungin.

60. The method of claim 54, wherein the at least one anti-viral agent comprises at least one of combivir, boceprevir, abacavir, docosanol, aciclovir, didanosine, cidofovir, acyclovir, delavirdine, adefovir, amantadine, amprenavir, arbidol, darunavir atazanavir, atripla, zanamivir, or oseltamivir.

61. The method of claim 54, wherein the at least one homeopathic agent comprises at least one of traumeel, blue green algae, placenta, vitamin E, omega-3 fatty acids, lemongrass oil, and/or cedar oil.

62. The method of claim 40, wherein administration is by at least one route selected from the group consisting of injection, oral administration, inhalation, topical application, and rectal administration.

63. The method of claim 62, wherein administration is by at least one route selected from the group consisting of injection, and oral administration.

* * * * *